United States Patent
Kraus et al.

(10) Patent No.: US 10,729,753 B2
(45) Date of Patent: *Aug. 4, 2020

(54) COMPOSITIONS AND METHODS FOR TREATMENT OF HOMOCYSTINURIA

(71) Applicant: The Regents of the University of Colorado, a Body Corporate, Denver, CO (US)

(72) Inventors: Jan P. Kraus, Littleton, CO (US); Tomas Majtan, Aurora, CO (US); Erez Bublil, Ets Efraim (IL)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/243,295

(22) Filed: Jan. 9, 2019

(65) Prior Publication Data
US 2019/0125845 A1    May 2, 2019

Related U.S. Application Data

(60) Continuation of application No. 15/492,671, filed on Apr. 20, 2017, now Pat. No. 10,265,387, which is a continuation of application No. 14/935,690, filed on Nov. 9, 2015, now Pat. No. 9,675,678, which is a continuation-in-part of application No. 14/687,389, filed on Apr. 15, 2015, now Pat. No. 9,447,406, which is a division of application No. 13/803,804, filed on Mar. 14, 2013, now Pat. No. 9,034,318.

(60) Provisional application No. 61/758,138, filed on Jan. 29, 2013.

(51) Int. Cl.
| | | |
|---|---|---|
| *A61K 38/51* | (2006.01) |
| *A61K 31/385* | (2006.01) |
| *A61K 31/198* | (2006.01) |
| *A61K 47/60* | (2017.01) |
| *C12N 9/96* | (2006.01) |
| *C12N 9/88* | (2006.01) |
| *A61K 45/06* | (2006.01) |
| *A61K 9/00* | (2006.01) |
| *A61K 31/205* | (2006.01) |

(52) U.S. Cl.
CPC ............ *A61K 38/51* (2013.01); *A61K 9/0019* (2013.01); *A61K 31/198* (2013.01); *A61K 31/205* (2013.01); *A61K 31/385* (2013.01); *A61K 45/06* (2013.01); *A61K 47/60* (2017.08); *C12N 9/88* (2013.01); *C12N 9/96* (2013.01); *C12Y 402/01022* (2013.01); *A61K 2300/00* (2013.01)

(58) Field of Classification Search
CPC ...... A61K 9/0019; A61K 45/06; A61K 38/51; A61K 31/205; A61K 2300/00; A61K 31/198; A61K 31/385; A61K 47/60; C12N 9/88; C12N 9/96; C12Y 402/01022
See application file for complete search history.

(56) References Cited

U.S. PATENT DOCUMENTS

| | | | |
|---|---|---|---|
| 5,523,225 A | 6/1996 | Kraus | |
| 5,635,375 A | 6/1997 | Kraus et al. | |
| 5,643,575 A | 7/1997 | Martinez et al. | |
| 5,730,990 A | 3/1998 | Greenwald | |
| 5,902,588 A | 5/1999 | Greenwald | |
| 5,919,455 A | 7/1999 | Greenwald | |
| 6,113,906 A | 9/2000 | Greenwald | |
| 6,153,655 A | 11/2000 | Martinez | |
| 6,177,087 B1 | 1/2001 | Greenwald | |
| 7,485,307 B2 | 2/2009 | Kraus et al. | |
| 8,007,787 B2 | 8/2011 | Kraus | |
| 9,034,318 B2 | 5/2015 | Kraus et al. | |
| 9,447,406 B2 | 9/2016 | Kraus et al. | |
| 9,675,678 B2 | 6/2017 | Kraus et al. | |
| 10,265,387 B2 * | 4/2019 | Kraus .................. | A61K 9/0019 |
| 2013/0251700 A1 | 9/2013 | Carrillo et al. | |
| 2017/0065687 A1 | 3/2017 | Kraus et al. | |
| 2018/0318404 A1 * | 11/2018 | Kraus .................. | A61K 9/0019 |

FOREIGN PATENT DOCUMENTS

| | | |
|---|---|---|
| EP | 1 396 537 A1 | 9/2002 |
| EP | 1396537 | 3/2004 |
| EP | 1396537 A1 | 3/2004 |
| WO | 03/106971 A2 | 12/2003 |
| WO | 2003/106971 A2 | 12/2003 |
| WO | 03106971 A2 | 12/2003 |
| WO | 2012/001336 | 1/2012 |
| WO | 2013/148580 | 10/2013 |
| WO | 2014/120770 | 7/2014 |
| WO | 2018195006 A1 | 10/2018 |

OTHER PUBLICATIONS

Ding et al., Bioconjugated PLGA-4-arm-PEG branched polymeric nanoparticles as novel tumor targeting carriers. Nanotechnology, 2011, 165101: 12 pages. (Year: 2011).*
Kim et al., Functional modeling of vitamin responsiveness in yeast: a common pyridoxine-responsive cystathionine b-synthase mutation in homocystinuria. Human Mol. Genet., 1997, vol. 6(13); 2213-2221. (Year: 1997).*
Frank, N. et al. "Solvent-Accessinle Cysteines in Human Cystathionine β-Synthase: Crucial Role of Cysteine 431 in S-Adenosyl-L-methionine Binding" (2006) Biochemistry 45:11021-11029.
Examination report No. 2 for standard patent application issued Jun. 14, 2019 in corresponding Australia application 2014212471, entitled "Compositions and Methods for Treatment of Homocystinuria".

(Continued)

*Primary Examiner* — Ganapathirama Raghu
(74) *Attorney, Agent, or Firm* — DT Ward, PC; Donna T. Ward; Samuel A. McMahon

(57) ABSTRACT

Provided herein are improved compositions and methods for enzyme replacement therapy using modified human cystathionine beta synthase (CBS) in the treatment of homocystinuria and related diseases and disorders.

23 Claims, 13 Drawing Sheets

Specification includes a Sequence Listing.

(56) References Cited

OTHER PUBLICATIONS

Smith & Waterman, "Comparison of biosequences" Adv. Appl. Math. 2(4):482-489 (Dec. 1981).
Sokolova et al., "Cystathionine beta-synthase deficiency in Central Europe: discrepancy between biochemical and molecular genetic screening for homocystinuric alleles." Hum Mutat.18(6):548-9 (Dec. 2001).
Stabler et al., "Elevated plasma total homocysteine in severe methionine adenosyltranferase I/III deficiency." Metabolism, 51(8):981-88 (Aug. 2002).
Tan et al., "Polyethylene Glycol Conjugation of Recombinant Methionase for Cancer Therapy," Protein Expression and Purification 12:45-52 (Feb. 1998).
Taoka et al., "Assignment of enzymatic functions to specific regions of the PLP-dependent heme protein cystathionine beta-synthase." Biochemistry 38(40):13155-61 (Sep. 1999).
Vargas et al., "Detection of c-type cytochromes using enhanced chemiluminescence." Anal. Biochem. 209(2):323-6 (Mar. 1993).
Volpe & Laster, "Transsulfuration in fetal and postnatal mammalian liver and brain. Cysthathionine synthase, its relation to hormonal influences and cystathionine.", Biol. Neonate 20(5):385-403 (1972).
Vugmeyster et al., "Pharmacokinetics and toxicology of therapeutic proteins: Advances and challenges." World Journal of Biological Chemistry 3(4):73-92 (Apr. 2012).
Walter, et al., "Strategies for the treatment of cystathionine beta-synthase deficiency: the experience of the Willink Biochemical Genetics Unit over the past 30 years." Eur J Pediatr 157(Suppl 2):S71-6 (Apr. 1996).
Watanabe et al., "Mice deficient in cysthathionine beta-synthase: animal models for mild and severe homocyst(e) Inemia." Proc. Natl. Acad. Sci. U.S.A. 92(5):1585-89 (Feb. 1995).
Wilcken et al., "Homocystinuria—the effects of betaine in the treatment of patients not responsive to pyridoxine." N. Engl. J. Med. 309(8):448-53 (Aug. 1999).
Witkowski et al., "Conversion of a 13-Ketoacyl Synthase to a Malonyl Decarboxylase by Replacement of the Active-Site Cysteine with Glutamine." Biochemistry 38:11643-50 (Aug. 1999).
Yap et al., "Vascular outcome in patients with homocystinuria due to cystathionine beta-synthase deficiency treated chronically: a Multicenter observational study." Arterioscler. Thromb. Vasc. Biol. 21(12):2080-85 (Dec. 2001).
International Search Report from International Application No. PCT/US2014/013602, dated Jun. 17, 2014, pp. 1-6.
Allen et al., "Serum betaine, N,N-dimethylglycine and N-methylglycine levels in patients with cobalamin and folate deficiency and related inborn errors of metabolism." Metabolism 42(11)1448-60. (Nov. 1993).
Altschul et al., "Gapped BLAST and PSI-BLAST: a new generation of protein database search programs." Nucleic Acids Res. 25(17)(17):3389-3402 (Sep. 1997).
Altschul et al., "Basic local alignment search tool." J. Mol. Biol. 215(3):403-10 (Oct. 1990).
Barber & Spaeth, "The successful treatment of homocystinuria with pyridoxine."J. Pediatr. 75(3):463-78 (Sep. 1969).
Carson & Neill, "Metabolic abnormalities detected in a survey of mentally backward individuals in Northern Ireland." Arch. Dis. Child 37(195):505-13 (Oct. 1962).
D'Souza et al., "Pharmaceutical amyloidosis associated with subcutaneous insulin and enfuvirtide administration." Amyloid 21(2):71-75 (Jun. 2014; epub Jan. 22, 2014).
El-Sayed et al., "PLP-dependent enzymes: a potent therapeutic approach to cancer and cardiovascular diseases," Targets in gene therapy, Prof. Yongping You (Ed.), 307-540-2, In Tech (Aug. 2011).
Finkelstein, "Methionine metabolism in mammals." J. Nutr. Biochem. 1(5):228-37 (May 1990).
Frank et al., "Purification and characterization of the wild type and truncated human cystathionine beta-synthase enzymes expressed in *E.coli*" Archives of Biochemistry and Biophysics, 470(1): 64-72 (Nov. 2007).
Frank et al., "Solvent-accessible cysteines in human cystathionine beta-synthase: crucial role of cysteine 431 in S-adenosyl-L-methionine binding." Biochemistry 45(36):11021-29 (Sep. 2006).
Gaustadnes et al., "Prevalence of congenital homocystinuria in Denmark." N Engl J Med. 340(19):1513 (May 1999).
Gupta et al., "Mouse models of cystathionine beta-synthase deficiency reveal significant threshold effects of hyperhomocysteinemia." FASEB J. 23(3):883-93 (Mar. 2009).
Gupta et al., "Cysthathionine beta-synthase-deficient mice thrive on a low-methionine diet." FASEB J. 28(2):781-90 (Feb. 2014).
Harris & Chess "Effect of PEGYLATION on Pharmaceuticals" Nature Reviews. Drug Discovery 2(3):214-21 (Mar. 2003).
Henikoff & Henikoff, "Amino acid substitution matrices from protein blocks." Proc. Natl. Acad. Sci. USA 89:10915-919 (Nov. 1989).
Jakubowski et al., "Mutations in cystathionine beta-synthase or methylenetetrahydrofolate reductase gene increase N-homocysteinylated protein levels in humans." FASEB J 22(12): 4071-6 (Aug. 2008).
Janosik et al., "Crystallization and preliminary X-ray diffraction analysis of the active core of human recombinant human cystathionine 13-synthase: an enzyme involved in vascular disease." Acta Cryst. D57:289-291 (Feb. 2001).
Kang et al., "Emerging PEGylated drugs." Expert opinion on emerging drugs 14:363-380 (Jun. 2009).
Kitano, "Biological robustness." Nature Reviews Genetics, 5(11):826-37 (Nov. 2004).
Komrower et al., "Dietary treatment of homocystinuria." Arch. Dis. Child 41(220):666-71(Dec. 1966).
Kozich & Kraus, "Screening for mutations by expressing patient cDNA segments in *E. coli*: homocystinuria due to cystathionine beta-synthase deficiency." Hum. Mutation 1:113-23 (Apr. 1992).
Kraus, "Cystathionine beta-synthase (human)." Methods Enzymol. 143:388-94 (1987).
Kraus & Rosenberg, "Cystathionine beta-synthase from human liver: improved purification scheme and additional characterization of the enzyme in crude and pure form." Arch. Biochem. Biophys. 222(1):44-52 (Apr. 1983).
Kraus & Kozich, "Cystathionine beta-synthase and its deficiency." In Homocysteine in health and disease. J.D. Carmel R, ed. (New York: Cambridge University Press), pp. 223-243 (2001).
Levy "Physician's Guide to the Homocystinurias" published by the National Organization for Rare Disorders, pp. 1-8 (2010).
Li & Stewart, "Homocystinuria and psychiatric disorder: a case report." Pathology 31(3):221-24 (Aug. 1999).
Linnebank et al., "High prevalence of the I278T mutation of the human cystathionine beta-synthase detected by a novel screening application." Thromb Haemost. 85(6):986-88 (Jun. 2001).
Linnebank et al., "Isolated thrombosis due to the cystathionine beta-synthase mutation c.833T>C (1278T)." J. Inherited Metabol. Dis. 26(5):509-11 (Jun. 2003).
Lowry et al., "Protein measurement with the Folin phenol reagent." J. Biol. Chem. 193(1):265-75 (May 1951).
Maclean et al., "High homocysteine and thrombosis without connective tissue disorders are associated with a novel class of cystathionine beta-synthase (CBS) mutations." Hum. Mutat. 19(6):641-55 (Jun. 2002).
Maclean et al., "Cystathionine beta-synthase null homocystinuric mice fail to exhibit altered hemostasis or lowering of plasma homocysteine in response to betaine treatment." Mol. Genet. Metab 101(2-3):163-71 (Oct.-Nov. 2010).
Maclean et al., "A novel trangenic mouse model of CBS-deficient homocystinuria does not incur hepatic steatosis or fibrosis and exhibits a hypercoagulative phenotype that is ameliorated by betaine treatment." Mol. Genet. Metab. 101 (2-3):153-62 (Oct.-Nov. 2010).
Maclean et al., "Cystathionine protects against endoplasmic reticulum stress-induced lipid accumulation, tissue injury, and apoptotic cell death." J. Biol. Chem. 287(38):31994-32005 (Sep. 2012).
Majtan et al., "Rescue of cystathionine beta-synthase (CBS) mutants with chemical chaperones: purification and characterization of eight CBS mutant enzymes." J Biol Chem. 285(21):15866-73 (Mar. 2010).
Mansoor et al., "Redox status and protein binding of plasma homocysteine and other aminothiols in patients with early-onset

(56) References Cited

OTHER PUBLICATIONS peripheral vascular disease, homocysteine and peripheral vascular disease." Arterioscler Thromb Vasc Biol, 15(2):232-40 (Feb. 1995).
Mansoor et al., "Determination of the in vivo redox status of cysteine, cysteinylglycine, homocysteine, and gluthathione in human plasma." Anal. Biochem. 200(2)218-29 (Feb. 1992).
Canadian Office Action for corresponding Canadian Application 2,898,772 entitled "Cystathionine Beta-Synthase Enzyme Fore Treatment of Homocystinuria" dated Oct. 18, 2019.
Australian Examination Report 1 received in corresponding Australian Application No. 2014212471 entitled "Cystathionine Beta-Synthase Enzyme for Treatment of Homocystinuria" dated Feb. 1, 2019.
Frank et al, "Solvent-Accessible Cysteines in Human Cystathionine β-Synthase: Crucial Role of Cysteine 431 in S-Adenosyl-L-methionine Binding", Biochemistry, 2006, vol. 45, pp. 11021-11029.
Meier et al., "Structure of human cystathionine 13-synthase: a unique pyridoxal 5' -phosphate-dependent heme protein." EMBO 20(15):3910-16 (Aug. 2001).
Melenovska et al., "Chaperone therapy for homocystinuria: the rescue of CBS mutations by heme arginate." J. Inherit. Metab. Dis. 38(2); 284-297 (Mar. 2015).
Miles & Kraus, "Cystathionine beta-synthase: structure, function, regulation, and location of homocystinuria-causing mutations." J. Biol. Chem. 279(29):29871-74 (Jul. 2004).
Mudd et al., "Homocystinuria: An enzymatic defect." Science 143(3613):1443-45 (Mar. 1964).
Mudd et al., "The natural history of homocystinuria due to cystathionine beta-synthase deficiency." Am. J. Hum. Genet. 37(1):1-31 (Jan. 1985).
Mudd et al., "Homocysteine and its disulfide derivatives: A suggested consensus terminology." Arterioscler. Thromb. Vasc. Biol. 20:1704-1706 (Jul. 2000).
Mudd et al., "Disorders of Transsulfuration." In the Metabolic and molecular bases of inherited disease. C.R. Scriver, A.L. Beudet, W.S. Sly, V. D., C. B., K.K. W., and V. B., eds. (New York: McGraw-Hill), pp. 2007-2056 (2001).
Munke et al., "The gene for cystathionine beta-synthase (CBS) maps to the subtelomeric region on human chromosome 21q and to proximal mouse chromosome 17." Am. J. Hum. Genet. 42(4):550-59 (Apr. 1988).
Needleman & Wunsch, "A general method applicable to the search for similarities in the amino acid sequence of two proteins." J. Mol. Biol. 48(3):443-53 (Mar. 1970).
Pearson & Lipman, "Improved tools for biological sequence comparison" Proc. Nat'l. Acad. Sci. USA 85 (8):2444-2448 (Apr. 1988).

Picker & Levy, "Homocystinuria Caused by Cystathionine Beta-Synthase Deficiency." In GeneReviews. R.A. Pagon, M.P. Adam, T.D. Bird, C.R. Dolan, C.T. (Jan. 2004).
Refsum et al., "Facts and recommendations about total homocysteine determinations: an expert opinion." Clin. Chem. 50:3-32 (Jan. 2004).
Seffernick et al., "Melamine Deaminase and Atrazine Chlorohydrolase: 98 Percent Identical but Functionally Different." J. Bacterial. 183(8):2405-10 (April 200.
Skovby et al., "Assignment of the genes for cystathionine beta-synthase to human chromosome 21 in somatic cell hybrids." Hum. Genet. 65(3):291-94 (Apr. 1984).
Mansoor et al., "Redox status and protein binding of plasma homocysteine and other aminothoils in patients with homocystinuria." Metabolism, 42(11):1481-85 (Nov. 193).—Abstract submitted.
Pasut & Veronese, "State of the art in PEGylation: The great versatility achieved after forty years of research" Journal of Controlled Release, 161:461-72 (2012, Epub Nov. 7, 2011).
Pasut & Veronese, "PEGylation for improving the effectiveness of therapeutic biomolecules" Drugs of Today 45(9): 687-95 (2009).
Maclean, Kenneth N. et al. "A novel transgenic mouse model of CBS-deficient homocystinuria does not incur hepatic steatosis or fibrosis and exhibits a hypercoagulative phenotype that is ameliorated by betaine treatment", Mol Genet Metab. Oct. 2010; 101(2-3): pp. 153-162.
English Translation of Office Action received in corresponding Japanese Application No. 2015-555429 dated Sep. 29, 2017.
Ohja S et al: "Effects of Heme Ligand Mutations Including a Pathogenic Variant, H65R, on the Properties of Human Cystathionine Beta-Synthase", Biochemistry, Americal Chemical Society, US, vol. 41, No. 14, Apr. 9, 2002, pp. 4649-4654.
Extended European Search Report received in corresponding EP application No. 17172478.4 dated Dec. 11, 2017.
Office Action with English translation received for co-pending Japanese application No. 2015555429 dated Apr. 23, 2018.
Office Action with English translation received for co-pending Chinese application No. 201480006554.0 dated Apr. 26, 2018.
Office Action recieved for co-pending Israel application No. 239783 dated Jun. 26, 2018.
Extended European Search Report dated Apr. 15, 2019 in Application No. 16864878.0, entitled: Compositions and Methods for Treatment of Homocystinuria.
Bublil, E. M. et al. "Enzyme Replacement with PEGylated Cystathionine Beta-synthase Ameliorates Homocystinuria in Murine Model" The Journal of Clinical Investigation, 2016; 126(6):2372-2384.
Majtan, T. et al. "Pharmacokinetics and Pharmacodynamics of PEGylated Truncated Human Cystathionine Beta-synthase for Treatment of Homocystinuria" Life Sciences, 2018, vol. 200, p. 15-25.

\* cited by examiner

SEQUENCE LISTING

<160> NUMBER OF SEQ ID NOS: 16

<210> SEQ ID NO 1
<211> LENGTH: 1656
<212> TYPE: DNA
<213> ORGANISM: Homo sapiens

<400> SEQUENCE: 1

```
atgccgtcag aaaccccgca ggcagaagtg ggtccgacgg gttgcccgca ccgtagcggt      60
ccgcattctg caaaaggcag tctggaaaaa ggttccccgg aagataaaga agccaaagaa     120
ccgctgtgga ttcgtccgga cgcaccgtca cgctgtacct ggcagctggg tcgtccggca     180
agcgaatctc cgcatcacca tacggctccg gcgaaaagtc cgaaaattct gccggatatc     240
ctgaagaaaa ttggtgacac cccgatggtt cgtatcaaca aaatcggcaa aaaattcggt     300
ctgaaatgcg aactgctggc taaatgtgaa tttttcaatg cgggcggttc cgtgaaagat     360
cgtatctcac tgcgcatgat tgaagatgct gaacgcgacg gcaccctgaa accgggtgat     420
acgattatcg aaccgacctc tggcaacacg ggtatcggtc tggcactggc ggcggcagtc     480
cgtggttatc gctgcattat cgtgatgccg gaaaaaatga gctctgaaaa agttgatgtc     540
ctgcgtgctc tgggcgcgga aattgttcgt accccgacga atgcccgctt cgacagtccg     600
gaatcccatg tgggtgttgc atggcgcctg aaaaacgaaa tcccgaattc gcacattctg     660
gatcagtatc gtaacgctag caatccgctg gcgcattacg ataccacggc cgacgaaatc     720
ctgcagcaat gtgatggcaa actggacatg ctggtcgctt ctgtgggtac cggcggtacc     780
attacgggca tcgcgcgtaa actgaaagaa aaatgcccgg gctgtcgcat tatcggtgtg     840
gatccggaag gcagtattct ggcggaaccg gaagaactga accagaccga acaaaccacg     900
tatgaagttg aaggcatcgg ttacgatttt attccgaccg tcctggatcg cacggtggtt     960
gacaaatggt tcaaaagcaa tgacgaagaa gcctttacct tcgcacgtat gctgatcgct    1020
caggaaggtc tgctgtgcgg tggttcagca ggttcgacgg tcgcagtggc agttaaagct    1080
gcgcaggaac tgcaagaagg tcaacgttgt gtcgtgattc tgccggattc tgttcgcaac    1140
tacatgacca aatttctgag tgaccgttgg atgctgcaaa aaggcttcct gaaagaagaa    1200
gatctgaccg agaaaaaacc gtggtggtgg cacctgcgcg tgcaggaact gggtctgtcc    1260
gcaccgctga ccgttctgcc gaccatcacg tgcggccata cgattgaaat cctgcgtgaa    1320 aaaggtttg atcaggcccc ggttgtcgac gaagcaggcg tgattctggg tatggttacc    1380
ctgggtaaca tgctgagttc cctgctggcg ggcaaagtgc aaccgagcga tcaggttggt    1440
aaagtcatct acaaacaatt caaacagatt cgtctgaccg atacgctggg ccgcctgtcg    1500
cacatcctgg aaatggacca tttcgcgctg gttgtgcacg aacagattca ataccatagc    1560 accgcaaat catcgcagcg ccaaatggtc tttggtgtcg tgacggccat tgatctgctg    1620
aatttcgtgg ccgcacaaga acgtgaccag aaataa                              1656
```

```
<210> SEQ ID NO 2
<211> LENGTH: 551
<212> TYPE: PRT
<213> ORGANISM: Homo sapiens

<400> SEQUENCE: 2

Met Pro Ser Glu Thr Pro Gln Ala Glu Val Gly Pro Thr Gly Cys Pro
1               5                   10                  15

His Arg Ser Gly Pro His Ser Ala Lys Gly Ser Leu Glu Lys Gly Ser
            20                  25                  30

Pro Glu Asp Lys Glu Ala Lys Glu Pro Leu Trp Ile Arg Pro Asp Ala
        35                  40                  45

Pro Ser Arg Cys Thr Trp Gln Leu Gly Arg Pro Ala Ser Glu Ser Pro
50                  55                  60

His His His Thr Ala Pro Ala Lys Ser Pro Lys Ile Leu Pro Asp Ile
65                  70                  75                  80

Leu Lys Lys Ile Gly Asp Thr Pro Met Val Arg Ile Asn Lys Ile Gly
                85                  90                  95

Lys Lys Phe Gly Leu Lys Cys Glu Leu Leu Ala Lys Cys Glu Phe Phe
            100                 105                 110

Asn Ala Gly Gly Ser Val Lys Asp Arg Ile Ser Leu Arg Met Ile Glu
        115                 120                 125

Asp Ala Glu Arg Asp Gly Thr Leu Lys Pro Gly Asp Thr Ile Ile Glu
130                 135                 140

Pro Thr Ser Gly Asn Thr Gly Ile Gly Leu Ala Leu Ala Ala Ala Val
145                 150                 155                 160

Arg Gly Tyr Arg Cys Ile Ile Val Met Pro Glu Lys Met Ser Ser Glu
                165                 170                 175

Lys Val Asp Val Leu Arg Ala Leu Gly Ala Glu Ile Val Arg Thr Pro
            180                 185                 190

Thr Asn Ala Arg Phe Asp Ser Pro Glu Ser His Val Gly Val Ala Trp
        195                 200                 205

Arg Leu Lys Asn Glu Ile Pro Asn Ser His Ile Leu Asp Gln Tyr Arg
210                 215                 220

Asn Ala Ser Asn Pro Leu Ala His Tyr Asp Thr Thr Ala Asp Glu Ile
225                 230                 235                 240

Leu Gln Gln Cys Asp Gly Lys Leu Asp Met Leu Val Ala Ser Val Gly
                245                 250                 255

Thr Gly Gly Thr Ile Thr Gly Ile Ala Arg Lys Leu Lys Glu Lys Cys
            260                 265                 270

Pro Gly Cys Arg Ile Ile Gly Val Asp Pro Glu Gly Ser Ile Leu Ala
        275                 280                 285

Glu Pro Glu Glu Leu Asn Gln Thr Glu Gln Thr Thr Tyr Glu Val Glu
290                 295                 300

Gly Ile Gly Tyr Asp Phe Ile Pro Thr Val Leu Asp Arg Thr Val Val
305                 310                 315                 320

Asp Lys Trp Phe Lys Ser Asn Asp Glu Glu Ala Phe Thr Phe Ala Arg
                325                 330                 335

Met Leu Ile Ala Gln Glu Gly Leu Leu Cys Gly Gly Ser Ala Gly Ser
            340                 345                 350

Thr Val Ala Val Ala Val Lys Ala Ala Gln Glu Leu Gln Glu Gly Gln
        355                 360                 365

Arg Cys Val Val Ile Leu Pro Asp Ser Val Arg Asn Tyr Met Thr Lys
370                 375                 380
```

```
Phe Leu Ser Asp Arg Trp Met Leu Gln Lys Gly Phe Leu Lys Glu Glu
385                 390                 395                 400

Asp Leu Thr Glu Lys Lys Pro Trp Trp Trp His Leu Arg Val Gln Glu
            405                 410                 415

Leu Gly Leu Ser Ala Pro Leu Thr Val Leu Pro Thr Ile Thr Cys Gly
        420                 425                 430

His Thr Ile Glu Ile Leu Arg Glu Lys Gly Phe Asp Gln Ala Pro Val
            435                 440                 445

Val Asp Glu Ala Gly Val Ile Leu Gly Met Val Thr Leu Gly Asn Met
450                 455                 460

Leu Ser Ser Leu Leu Ala Gly Lys Val Gln Pro Ser Asp Gln Val Gly
465                 470                 475                 480

Lys Val Ile Tyr Lys Gln Phe Lys Gln Ile Arg Leu Thr Asp Thr Leu
            485                 490                 495

Gly Arg Leu Ser His Ile Leu Glu Met Asp His Phe Ala Leu Val Val
            500                 505                 510

His Glu Gln Ile Gln Tyr His Ser Thr Gly Lys Ser Ser Gln Arg Gln
            515                 520                 525

Met Val Phe Gly Val Val Thr Ala Ile Asp Leu Leu Asn Phe Val Ala
            530                 535                 540

Ala Gln Glu Arg Asp Gln Lys
545                 550

<210> SEQ ID NO 3
<211> LENGTH: 413
<212> TYPE: PRT
<213> ORGANISM: Artificial Sequence
<220> FEATURE:
<223> OTHER INFORMATION: Synthetic

<400> SEQUENCE: 3

Met Pro Ser Glu Thr Pro Gln Ala Glu Val Gly Pro Thr Gly Cys Pro
1               5                   10                  15

His Arg Ser Gly Pro His Ser Ala Lys Gly Ser Leu Glu Lys Gly Ser
            20                  25                  30

Pro Glu Asp Lys Glu Ala Lys Glu Pro Leu Trp Ile Arg Pro Asp Ala
        35                  40                  45

Pro Ser Arg Cys Thr Trp Gln Leu Gly Arg Pro Ala Ser Glu Ser Pro
    50                  55                  60

His His His Thr Ala Pro Ala Lys Ser Pro Lys Ile Leu Pro Asp Ile
65                  70                  75                  80

Leu Lys Lys Ile Gly Asp Thr Pro Met Val Arg Ile Asn Lys Ile Gly
                85                  90                  95

Lys Lys Phe Gly Leu Lys Cys Glu Leu Leu Ala Lys Cys Glu Phe Phe
            100                 105                 110

Asn Ala Gly Gly Ser Val Lys Asp Arg Ile Ser Leu Arg Met Ile Glu
        115                 120                 125

Asp Ala Glu Arg Asp Gly Thr Leu Lys Pro Gly Asp Thr Ile Ile Glu
    130                 135                 140

Pro Thr Ser Gly Asn Thr Gly Ile Gly Leu Ala Leu Ala Ala Ala Val
145                 150                 155                 160

Arg Gly Tyr Arg Cys Ile Ile Val Met Pro Glu Lys Met Ser Ser Glu
                165                 170                 175

Lys Val Asp Val Leu Arg Ala Leu Gly Ala Glu Ile Val Arg Thr Pro
            180                 185                 190
```

Thr Asn Ala Arg Phe Asp Ser Pro Glu Ser His Val Gly Val Ala Trp
    195                 200                 205

Arg Leu Lys Asn Glu Ile Pro Asn Ser His Ile Leu Asp Gln Tyr Arg
    210                 215                 220

Asn Ala Ser Asn Pro Leu Ala His Tyr Asp Thr Thr Ala Asp Glu Ile
225                 230                 235                 240

Leu Gln Gln Cys Asp Gly Lys Leu Asp Met Leu Val Ala Ser Val Gly
                245                 250                 255

Thr Gly Gly Thr Ile Thr Gly Ile Ala Arg Lys Leu Lys Glu Lys Cys
            260                 265                 270

Pro Gly Cys Arg Ile Ile Gly Val Asp Pro Glu Gly Ser Ile Leu Ala
        275                 280                 285

Glu Pro Glu Glu Leu Asn Gln Thr Glu Gln Thr Thr Tyr Glu Val Glu
    290                 295                 300

Gly Ile Gly Tyr Asp Phe Ile Pro Thr Val Leu Asp Arg Thr Val Val
305                 310                 315                 320

Asp Lys Trp Phe Lys Ser Asn Asp Glu Glu Ala Phe Thr Phe Ala Arg
                325                 330                 335

Met Leu Ile Ala Gln Glu Gly Leu Leu Cys Gly Gly Ser Ala Gly Ser
            340                 345                 350

Thr Val Ala Val Ala Val Lys Ala Ala Gln Glu Leu Gln Glu Gly Gln
        355                 360                 365

Arg Cys Val Val Ile Leu Pro Asp Ser Val Arg Asn Tyr Met Thr Lys
    370                 375                 380

Phe Leu Ser Asp Arg Trp Met Leu Gln Lys Gly Phe Leu Lys Glu Glu
385                 390                 395                 400

Asp Leu Thr Glu Lys Lys Pro Trp Trp Trp His Leu Arg
                405                 410

<210> SEQ ID NO 4
<211> LENGTH: 1242
<212> TYPE: DNA
<213> ORGANISM: Artificial Sequence
<220> FEATURE:
<223> OTHER INFORMATION: Synthetic

<400> SEQUENCE: 4

```
atgccgtcag aaaccccgca ggcagaagtg ggtccgacgg gttgcccgca ccgtagcggt    60
ccgcattctg caaaaggcag tctggaaaaa ggttccccgg aagataaaga agccaaagaa   120
ccgctgtgga ttcgtccgga cgcaccgtca cgctgtacct ggcagctggg tcgtccggca   180
agcgaatctc cgcatcacca tacggctccg gcgaaaagtc cgaaaattct gccggatatc   240
ctgaagaaaa ttggtgacac cccgatggtt cgtatcaaca aaatcggcaa aaaattcggt   300
ctgaaatgcg aactgctggc taaatgtgaa tttttcaatg cgggcggttc cgtgaaagat   360
cgtatctcac tgcgcatgat tgaagatgct gaacgcgacg gcaccctgaa accgggtgat   420
acgattatcg aaccgacctc tggcaacacg ggtatcggtc tggcactggc ggcggcagtc   480
cgtggttatc gctgcattat cgtgatgccg aaaaaatga ctctgaaaa agttgatgtc   540 ctgcgtgctc tgggcgcgga aattgttcgt accccgacga atgcccgctt cgacagtccg   600
gaatcccatg tgggtgttgc atggcgcctg aaaaacgaaa tcccgaattc gcacattctg   660
gatcagtatc gtaacgctag caatccgctg gcgcattacg ataccacggc cgacgaaatc   720
ctgcagcaat gtgatggcaa actggacatg ctggtcgctt ctgtgggtac cggcggtacc   780
```

```
attacgggca tcgcgcgtaa actgaaagaa aaatgcccgg gctgtcgcat tatcggtgtg      840
gatccggaag gcagtattct ggcggaaccg gaagaactga accagaccga acaaaccacg      900
tatgaagttg aaggcatcgg ttacgatttt attccgaccg tcctggatcg cacggtggtt      960
gacaaatggt tcaaaagcaa tgacgaagaa gcctttacct tcgcacgtat gctgatcgct     1020
caggaaggtc tgctgtgcgg tggttcagca ggttcgacgg tcgcagtggc agttaaagct     1080
gcgcaggaac tgcaagaagg tcaacgttgt gtcgtgattc tgccggattc tgttcgcaac     1140
tacatgacca aatttctgag tgaccgttgg atgctgcaaa aaggcttcct gaaagaagaa     1200
gatctgaccg agaaaaaacc gtggtggtgg cacctgcgct aa                        1242
```

```
<210> SEQ ID NO 5
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 5
cgtagaattc acctttgccc gcatgctgat                                        30

<210> SEQ ID NO 6
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 6
tacgggtacc tcaacggagg tgccaccacc agggc                                  35

<210> SEQ ID NO 7
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 7
agtcgcccat ggcgtcagaa accccgcag                                         29

<210> SEQ ID NO 8
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 8
atcgcgctcg agttagcgca ggtgccacca c                                      31

<210> SEQ ID NO 9
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 9
ggagatatac catgccgtca gaaaccccgc                                        30

<210> SEQ ID NO 10
<211> LENGTH: 30
```

<212> TYPE: DNA
<213> ORGANISM: Artificial Sequence
<220> FEATURE:
<223> OTHER INFORMATION: Synthetic oligonucleotide

<400> SEQUENCE: 10
gcggggtttc tgacggcatg gtatatctcc                                    30

<210> SEQ ID NO 11
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 11
tgggtccgac gggtagcccg cac                                           23

<210> SEQ ID NO 12
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 12
gtgcgggcta cccgtcggac cca                                           23

<210> SEQ ID NO 13
<211> LENGTH: 413
<212> TYPE: PRT
<213> ORGANISM: Artificial Sequence
<220> FEATURE:
<223> OTHER INFORMATION: Truncated human C15S mutant CBS polypeptide

<400> SEQUENCE: 13

Met Pro Ser Glu Thr Pro Gln Ala Glu Val Gly Pro Thr Gly Ser Pro
1               5                   10                  15

His Arg Ser Gly Pro His Ser Ala Lys Gly Ser Leu Glu Lys Gly Ser
            20                  25                  30

Pro Glu Asp Lys Glu Ala Lys Glu Pro Leu Trp Ile Arg Pro Asp Ala
        35                  40                  45

Pro Ser Arg Cys Thr Trp Gln Leu Gly Arg Pro Ala Ser Glu Ser Pro
    50                  55                  60

His His His Thr Ala Pro Ala Lys Ser Pro Lys Ile Leu Pro Asp Ile
65                  70                  75                  80

Leu Lys Lys Ile Gly Asp Thr Pro Met Val Arg Ile Asn Lys Ile Gly
                85                  90                  95

Lys Lys Phe Gly Leu Lys Cys Glu Leu Leu Ala Lys Cys Glu Phe Phe
            100                 105                 110

Asn Ala Gly Gly Ser Val Lys Asp Arg Ile Ser Leu Arg Met Ile Glu
        115                 120                 125

Asp Ala Glu Arg Asp Gly Thr Leu Lys Pro Gly Asp Thr Ile Ile Glu
    130                 135                 140

Pro Thr Ser Gly Asn Thr Gly Ile Gly Leu Ala Leu Ala Ala Ala Val
145                 150                 155                 160

Arg Gly Tyr Arg Cys Ile Ile Val Met Pro Glu Lys Met Ser Ser Glu
                165                 170                 175

Lys Val Asp Val Leu Arg Ala Leu Gly Ala Glu Ile Val Arg Thr Pro
            180                 185                 190

```
Thr Asn Ala Arg Phe Asp Ser Pro Glu Ser His Val Gly Val Ala Trp
            195                 200                 205
Arg Leu Lys Asn Glu Ile Pro Asn Ser His Ile Leu Asp Gln Tyr Arg
        210                 215                 220
Asn Ala Ser Asn Pro Leu Ala His Tyr Asp Thr Thr Ala Asp Glu Ile
225                 230                 235                 240
Leu Gln Gln Cys Asp Gly Lys Leu Asp Met Leu Val Ala Ser Val Gly
                245                 250                 255
Thr Gly Gly Thr Ile Thr Gly Ile Ala Arg Lys Leu Lys Glu Lys Cys
            260                 265                 270
Pro Gly Cys Arg Ile Ile Gly Val Asp Pro Glu Gly Ser Ile Leu Ala
        275                 280                 285
Glu Pro Glu Glu Leu Asn Gln Thr Glu Gln Thr Thr Tyr Glu Val Glu
    290                 295                 300
Gly Ile Gly Tyr Asp Phe Ile Pro Thr Val Leu Asp Arg Thr Val Val
305                 310                 315                 320
Asp Lys Trp Phe Lys Ser Asn Asp Glu Glu Ala Phe Thr Phe Ala Arg
                325                 330                 335
Met Leu Ile Ala Gln Glu Gly Leu Leu Cys Gly Gly Ser Ala Gly Ser
            340                 345                 350
Thr Val Ala Val Ala Val Lys Ala Ala Gln Glu Leu Gln Glu Gly Gln
        355                 360                 365
Arg Cys Val Val Ile Leu Pro Asp Ser Val Arg Asn Tyr Met Thr Lys
    370                 375                 380
Phe Leu Ser Asp Arg Trp Met Leu Gln Lys Gly Phe Leu Lys Glu Glu
385                 390                 395                 400
Asp Leu Thr Glu Lys Lys Pro Trp Trp Trp His Leu Arg
                405                 410

<210> SEQ ID NO 14
<211> LENGTH: 1242
<212> TYPE: DNA
<213> ORGANISM: Artificial Sequence
<220> FEATURE:
<223> OTHER INFORMATION: Truncated human C15S mutant CBS Nucleotide

<400> SEQUENCE: 14
atgccgtcag aaaccccgca ggcagaagtg ggtccgacgg gtagcccgca ccgtagcggt      60
ccgcattctg caaaaggcag tctggaaaaa ggttccccgg aagataaaga agccaaagaa     120
ccgctgtgga ttcgtccgga cgcaccgtca cgctgtacct ggcagctggg tcgtccggca     180
agcgaatctc cgcatcacca tacggctccg gcgaaaagtc gaaaattct gccggatatc      240 ctgaagaaaa ttggtgacac cccgatggtt cgtatcaaca aaatcggcaa aaaattcggt     300
ctgaaatgcg aactgctggc taaatgtgaa tttttcaatg cgggcggttc cgtgaaagat     360
cgtatctcac tgcgcatgat tgaagatgct gaacgcgacg gcaccctgaa accgggtgat     420
acgattatcg aaccgacctc tggcaacacg gtatcggtc tggcactggc ggcggcagtc      480
cgtggttatc gctgcattat cgtgatgccg gaaaaatga gctctgaaaa agttgatgtc      540
ctgcgtgctc tgggcgcgga aattgttcgt accccgacga atgcccgctt cgacagtccg     600
gaatcccatg tgggtgttgc atggcgcctg aaaaacgaaa tcccgaattc gcacattctg     660
gatcagtatc gtaacgctag caatccgctg gcgcattacg ataccacggc cgacgaaatc     720
ctgcagcaat gtgatggcaa actggacatg ctggtcgctt ctgtgggtac cggcggtacc     780
attacgggca tcgcgcgtaa actgaaagaa aaatgcccgg gctgtcgcat tatcggtgtg     840
```

```
gatccggaag gcagtattct ggcggaaccg gaagaactga accagaccga acaaaccacg      900
tatgaagttg aaggcatcgg ttacgatttt attccgaccg tcctggatcg cacggtggtt      960
gacaaatggt tcaaaagcaa tgacgaagaa gcctttacct tcgcacgtat gctgatcgct     1020
caggaaggtc tgctgtgcgg tggttcagca ggttcgacgg tcgcagtggc agttaaagct     1080
gcgcaggaac tgcaagaagg tcaacgttgt gtcgtgattc tgccggattc tgttcgcaac     1140
tacatgacca aatttctgag tgaccgttgg atgctgcaaa aaggcttcct gaaagaagaa     1200
gatctgaccg agaaaaaacc gtggtggtgg cacctgcgct aa                        1242
```

<210> SEQ ID NO 15
<211> LENGTH: 1656
<212> TYPE: DNA
<213> ORGANISM: Artificial Sequence
<220> FEATURE:
<223> OTHER INFORMATION: Full length human C15S mutant CBS nucleotide

<400> SEQUENCE: 15

```
atgccgtcag aaaccccgca ggcagaagtg ggtccgacgg gtagcccgca ccgtagcggt       60
ccgcattctg caaaaggcag tctggaaaaa ggttccccgg aagataaaga agccaaagaa      120
ccgctgtgga ttcgtccgga cgcaccgtca cgctgtacct ggcagctggg tcgtccggca      180
agcgaatctc cgcatcacca tacggctccg gcgaaaagtc cgaaaattct gccggatatc      240
ctgaagaaaa ttggtgacac cccgatggtt cgtatcaaca aaatcggcaa aaaattcggt      300
ctgaaatgcg aactgctggc taaatgtgaa tttttcaatg cggcggttc cgtgaaagat       360 cgtatctcac tgcgcatgat tgaagatgct gaacgcgacg gcacccctgaa accgggtgat     420 acgattatcg aaccgacctc tggcaacacg ggtatcggtc tggcactggc ggcggcagtc      480
cgtggttatc gctgcattat cgtgatgccg gaaaaaatga gctctgaaaa agttgatgtc      540
ctgcgtgctc tgggcgcgga aattgttcgt accccgacga atgcccgctt cgacagtccg      600
gaatcccatg tgggtgttgc atggcgcctg aaaaacgaaa tcccgaattc gcacattctg      660
gatcagtatc gtaacgctag caatccgctg gcgcattacg ataccacggc cgacgaaatc      720
ctgcagcaat gtgatggcaa actggacatg ctggtcgctt ctgtgggtac cggcggtacc      780
attacgggca tcgcgcgtaa actgaaagaa aaatgcccgg gctgtcgcat tatcggtgtg      840
gatccggaag gcagtattct ggcggaaccg gaagaactga accagaccga acaaaccacg      900
tatgaagttg aaggcatcgg ttacgatttt attccgaccg tcctggatcg cacggtggtt      960
gacaaatggt tcaaaagcaa tgacgaagaa gcctttacct tcgcacgtat gctgatcgct     1020
caggaaggtc tgctgtgcgg tggttcagca ggttcgacgg tcgcagtggc agttaaagct     1080
gcgcaggaac tgcaagaagg tcaacgttgt gtcgtgattc tgccggattc tgttcgcaac     1140
tacatgacca aatttctgag tgaccgttgg atgctgcaaa aaggcttcct gaaagaagaa     1200
gatctgaccg agaaaaaacc gtggtggtgg cacctgcgcg tgcaggaact gggtctgtcc     1260
gcaccgctga ccgttctgcc gaccatcacg tgcggccata cgattgaaat cctgcgtgaa     1320
aaaggttttg atcaggcccc ggttgtcgac gaagcaggcg tgattctggg tatggttacc     1380
ctgggtaaca tgctgagttc cctgctggcg ggcaaagtgc aaccgagcga tcaggttggt     1440
aaagtcatct acaaacaatt caaacagatt cgtctgaccg atacgctggg ccgcctgtcg     1500
cacatcctgg aaatggacca tttcgcgctg gttgtgcacg aacagattca ataccatagc     1560
accggcaaat catcgcagcg ccaaatggtc tttggtgtcg tgacggccat tgatctgctg     1620
```
aatttcgtgg ccgcacaaga acgtgaccag aaataa                                          1656

<210> SEQ ID NO 16
<211> LENGTH: 551
<212> TYPE: PRT
<213> ORGANISM: Artificial Sequence
<220> FEATURE:
<223> OTHER INFORMATION: Full length human C15S mutant CBS polypeptide

<400> SEQUENCE: 16

```
Met Pro Ser Glu Thr Pro Gln Ala Glu Val Gly Pro Thr Gly Ser Pro
1               5                   10                  15

His Arg Ser Gly Pro His Ser Ala Lys Gly Ser Leu Glu Lys Gly Ser
            20                  25                  30

Pro Glu Asp Lys Glu Ala Lys Glu Pro Leu Trp Ile Arg Pro Asp Ala
        35                  40                  45

Pro Ser Arg Cys Thr Trp Gln Leu Gly Arg Pro Ala Ser Glu Ser Pro
    50                  55                  60

His His His Thr Ala Pro Ala Lys Ser Pro Lys Ile Leu Pro Asp Ile
65                  70                  75                  80

Leu Lys Lys Ile Gly Asp Thr Pro Met Val Arg Ile Asn Lys Ile Gly
                85                  90                  95

Lys Lys Phe Gly Leu Lys Cys Glu Leu Leu Ala Lys Cys Glu Phe Phe
            100                 105                 110

Asn Ala Gly Gly Ser Val Lys Asp Arg Ile Ser Leu Arg Met Ile Glu
        115                 120                 125

Asp Ala Glu Arg Asp Gly Thr Leu Lys Pro Gly Asp Thr Ile Ile Glu
    130                 135                 140

Pro Thr Ser Gly Asn Thr Gly Ile Gly Leu Ala Leu Ala Ala Ala Val
145                 150                 155                 160

Arg Gly Tyr Arg Cys Ile Ile Val Met Pro Glu Lys Met Ser Ser Glu
                165                 170                 175

Lys Val Asp Val Leu Arg Ala Leu Gly Ala Glu Ile Val Arg Thr Pro
            180                 185                 190

Thr Asn Ala Arg Phe Asp Ser Pro Glu Ser His Val Gly Val Ala Trp
        195                 200                 205

Arg Leu Lys Asn Glu Ile Pro Asn Ser His Ile Leu Asp Gln Tyr Arg
    210                 215                 220

Asn Ala Ser Asn Pro Leu Ala His Tyr Asp Thr Thr Ala Asp Glu Ile
225                 230                 235                 240

Leu Gln Gln Cys Asp Gly Lys Leu Asp Met Leu Val Ala Ser Val Gly
                245                 250                 255

Thr Gly Gly Thr Ile Thr Gly Ile Ala Arg Lys Leu Lys Glu Lys Cys
            260                 265                 270

Pro Gly Cys Arg Ile Ile Gly Val Asp Pro Glu Gly Ser Ile Leu Ala
        275                 280                 285

Glu Pro Glu Glu Leu Asn Gln Thr Glu Gln Thr Thr Tyr Glu Val Glu
    290                 295                 300

Gly Ile Gly Tyr Asp Phe Ile Pro Thr Val Leu Asp Arg Thr Val Val
305                 310                 315                 320

Asp Lys Trp Phe Lys Ser Asn Asp Glu Glu Ala Phe Thr Phe Ala Arg
                325                 330                 335

Met Leu Ile Ala Gln Glu Gly Leu Leu Cys Gly Gly Ser Ala Gly Ser
            340                 345                 350

Thr Val Ala Val Ala Val Lys Ala Ala Gln Glu Leu Gln Glu Gly Gln
```

-continued

```
              355                 360                 365
Arg Cys Val Val Ile Leu Pro Asp Ser Val Arg Asn Tyr Met Thr Lys
    370                 375                 380

Phe Leu Ser Asp Arg Trp Met Leu Gln Lys Gly Phe Leu Lys Glu Glu
385                 390                 395                 400

Asp Leu Thr Glu Lys Lys Pro Trp Trp Trp His Leu Arg Val Gln Glu
                405                 410                 415

Leu Gly Leu Ser Ala Pro Leu Thr Val Leu Pro Thr Ile Thr Cys Gly
                420                 425                 430

His Thr Ile Glu Ile Leu Arg Glu Lys Gly Phe Asp Gln Ala Pro Val
        435                 440                 445

Val Asp Glu Ala Gly Val Ile Leu Gly Met Val Thr Leu Gly Asn Met
    450                 455                 460

Leu Ser Ser Leu Leu Ala Gly Lys Val Gln Pro Ser Asp Gln Val Gly
465                 470                 475                 480

Lys Val Ile Tyr Lys Gln Phe Lys Gln Ile Arg Leu Thr Asp Thr Leu
                485                 490                 495

Gly Arg Leu Ser His Ile Leu Glu Met Asp His Phe Ala Leu Val Val
                500                 505                 510

His Glu Gln Ile Gln Tyr His Ser Thr Gly Lys Ser Ser Gln Arg Gln
        515                 520                 525

Met Val Phe Gly Val Val Thr Ala Ile Asp Leu Leu Asn Phe Val Ala
    530                 535                 540

Ala Gln Glu Arg Asp Gln Lys
545                 550
```

COMPOSITIONS AND METHODS FOR TREATMENT OF HOMOCYSTINURIA

CROSS-REFERENCE TO RELATED APPLICATIONS

This application is a continuation of U.S. application Ser. No. 15/492,671 (granted as U.S. Pat. No. 10,265,387) filed Apr. 20, 2017, which is a continuation of U.S. application Ser. No. 14/935,690 (granted as U.S. Pat. No. 9,675,678), filed Nov. 9, 2015, which is a continuation in part of U.S. application Ser. No. 14/687,389 (granted as U.S. Pat. No. 9,447,406), filed Apr. 15, 2015, which is a Divisional of U.S. application Ser. No. 13/803,804 (granted as U.S. Pat. No. 9,034,318), filed Mar. 14, 2013 which claims the priority to U.S. provisional application 61/758,138, filed Jan. 29, 2013; the contents of each of which are incorporated herein by reference in their entirety.

REFERENCE TO THE SEQUENCE LISTING

The present application is being filed along with a Sequence Listing in electronic format. The Sequence Listing is provided as a file entitled 20891003-USCON2_SEQLST.txt, created on Jan. 8, 2019 which is 27,035 bytes in size. The information in the electronic format of the sequence listing is incorporated herein by reference in its entirety.

FIELD OF THE INVENTION

The present invention generally relates to enzyme replacement therapy (ERT) using human Cystathionine Beta-Synthase (CBS), or a modified version thereof (e.g., human truncated CBS (htCBS) or a variant thereof), to significantly reduce serum homocysteine (Hcy) concentrations, and restore levels of its downstream metabolites such as cystathionine and cysteine. Further, ERT with CBS, htCBS or a modified version thereof can be used for treatment of diseases such as homocystinuria and homocysteine remethylation disorders.

BACKGROUND OF THE INVENTION

Cystathionine beta-synthase (CBS) is the first enzyme in the transsulfuration pathway, catalyzing the condensation of serine and homocysteine (Hcy) to cystathionine, which is then hydrolyzed to cysteine by Cystathionine Gamma Lyase (CGL). In systems biology, robustness of a biological system is defined as its ability to function properly in face of perturbations, and redundancy of elements in the system is one of the mechanisms by which such robustness is achieved (Kitano, H. 2004, Nature Reviews Genetics, 5:826-837). However, the biological transsulfuration system seems to largely lack redundancy of components, making this system prone to mutational perturbations. For example, the CBS enzyme is the only component that can process homocysteine to cystathionine. A limited system redundancy partly exists as homocysteine, the first metabolite that funnels into the pathway, can alternatively be converted to methionine through the remethylation pathway, thus relieving the homocysteine load. In addition, cysteine, a downstream product, can be obtained directly from diet. Nevertheless, these pathways are limited in their capacity to maintain normal levels of metabolites, and lack of CBS function has detrimental consequences for human patients if left untreated. Inactivation of CBS results in cystathionine beta-synthase-deficient homocystinuria (CBSDH), more commonly referred to as classical homocystinuria.

There exist limited therapeutic options to treat CBSDH and current treatment options reduce homocysteine but do not tend to normalize cystathionine (Cth) or cysteine (Cys) and thus these treatment options may be inadequate for providing robust and effective treatment options. Thus, there remains a need in the art for more effective treatment strategies for individuals with homocystinuria.

The present invention addresses this need by providing compositions and methods of using these compositions for the treatment of CBSDH.

SUMMARY OF THE INVENTION

The present disclosure provides compositions suitable for enzyme replacement therapy comprising human truncated cystathionine beta synthase (htCBS) and variants thereof which may also be PEGylated. The htCBS composition may be used to reduce homocysteine levels and raise levels of downstream metabolites cystathionine and cysteine, may be used to treat conditions and diseases such as homocystinuria (e.g., CBSDH) and homocysteine remethylation disorders and they also may be used to improve liver pathology.

Provided herein are methods for treating homocystinuria in a subject by administering to a subject a composition comprising an htCBS or htCBS mutant polypeptide. The htCBS or htCBS mutant polypeptide may be PEGylated with a low molecular weight or high molecular weight PEG. The htCBS or htCBS mutant polypeptide may be administered at a dose between 5 and 7.5 mg/kg and may be administered at least twice a week. Further, the htCBS or htCBS mutant polypeptide may be co-administered with betaine, or other known CBSDH therapies.

Provided herein are methods for increasing the amount of a metabolite such as, but not limited to, cystathionine and cysteine, in a subject by administering to a subject a composition comprising an htCBS or htCBS mutant polypeptide. The htCBS or htCBS mutant polypeptide may be PEGylated with a low molecular weight or high molecular weight PEG. The htCBS or htCBS mutant polypeptide may be administered at a dose between 5 and 7.5 mg/kg and may be administered at least twice a week. Further, the htCBS or htCBS mutant polypeptide may be co-administered with betaine. The amount of cystathionine may be increased to 0.005-0.35 uM. The amount of cysteine may be increased to above 140 uM (e.g., between 200 uM to 400 uM)

Provided herein are methods for decreasing the amount of a metabolite such as, but not limited to, homocysteine, methionine S-adenosyl homocysteine, and S-adenosyl methionine in a subject by administering to a subject a composition comprising an htCBS or htCBS mutant polypeptide. The htCBS or htCBS mutant polypeptide may be PEGylated with a low molecular weight or high molecular weight PEG. The htCBS or htCBS mutant polypeptide may be administered at a dose between 5 and 7.5 mg/kg and may be administered at least twice a week. Further, the htCBS or htCBS mutant polypeptide may be co-administered with betaine. The amount of homocysteine may be decreased to less than 100 uM (e.g., about 10 uM). The amount of methionine may be decreased to less than 50 uM (e.g., about 30 uM). The amount of S-adenosyl homocysteine may be decreased to less than 0.14 uM (e.g., about 0.015 uM)

Provided herein are methods for treating liver disease in a subject by administering to a subject a composition comprising an htCBS or htCBS mutant polypeptide. The htCBS or htCBS mutant polypeptide may be PEGylated with a low molecular weight or high molecular weight PEG. The htCBS or htCBS mutant polypeptide may be administered at a dose between 5 and 7.5 mg/kg and may be administered at least twice a week.

Additional embodiments of the present compositions and methods, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

BRIEF DESCRIPTION OF THE DRAWINGS

FIG. 1A shows enzyme retention time in plasma is maintained suggesting that rapid loss of activity in vivo is a result of clearance. FIG. 1B shows enzyme retention time is in vivo is enhanced for PEGylated htCBS and that PEGylation does not influence specific activity of the enzyme. Mouse #1 and Mouse #2 in FIG. 1B are also described as FIG. 1B in International Patent Publication No. WO2014120770, the contents of which are herein incorporated by reference in its entirety.

FIG. 5A is also described as FIG. 5A in International Patent Publication No. WO2014120770, the contents of which are herein incorporated by reference in its entirety. FIG. 5B is also described as FIG. 5B in International Patent Publication No. WO2014120770, the contents of which are herein incorporated by reference in its entirety.

FIG. 5C is also described as FIG. 5C in International Patent Publication No. WO2014120770, the contents of which are herein incorporated by reference in its entirety. FIG. 5F is also described as FIG. 6A in International Patent Publication No. WO2014120770, the contents of which are herein incorporated by reference in its entirety. FIG. 5G is also described as part of FIG. 7A and FIG. 7B in International Patent Publication No. WO2014120770, the contents of which are herein incorporated by reference in its entirety. FIG. 5H is also described as FIG. 6C in International Patent Publication No. WO2014120770, the contents of which are herein incorporated by reference in its entirety.

DETAILED DESCRIPTION

Figure 1A:
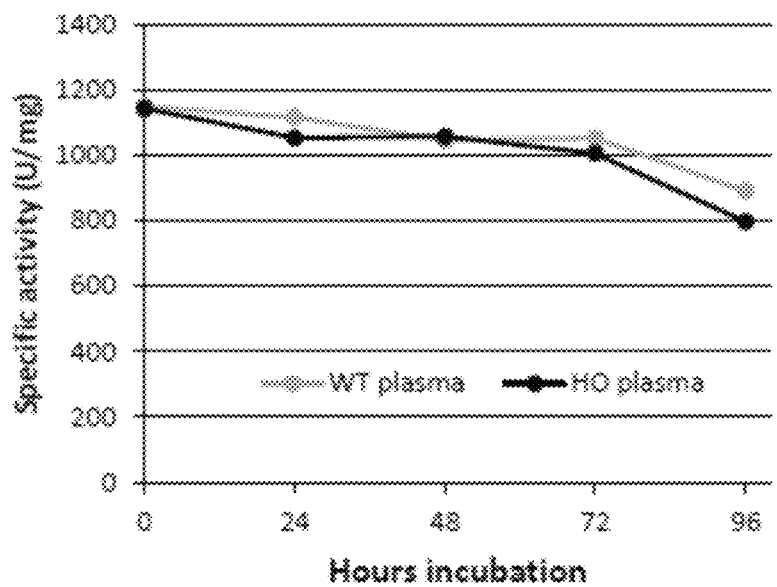
FIG. 1A-1B show enzyme retention in plasma and in vivo.

Provided herein are compositions and methods for treating cystathionine beta-synthase-deficient homocystinuria (CBSDH). As a non-limiting example, CBSDH may be treated by enzyme replacement of CBS or a variant thereof.

Inactivation of CBS results in cystathionine beta-synthase-deficient homocystinuria (CBSDH), more commonly referred to as classical homocystinuria. CBSDH is an autosomal recessive disorder characterized by markedly elevated plasma total homocysteine (tHcy) and methionine levels, and greatly reduced concentrations of cystathionine and cysteine; it is the most common sulfur-amino acid defect. If untreated, CBSDH results in diseases, disorders and/or conditions in a variety of different organ systems and severe phenotypic changes. Non-limiting examples of diseases, disorders and/or conditions from CBSDH include mental retardation, psychiatric disturbances, central nervous system problems including seizures, cardiovascular disease with a predisposition to thromboembolic complications resulting in a high rate of mortality in untreated and partially treated individuals, and a range of connective tissue disorders affecting the ocular system (e.g., progressive myopia and lens dislocation, ectopia lentis), and skeletal system (e.g., marfanoid habitus, osteoporosis, scoliosis, fine fair hair and brittle, thin skin).

There is a functional trichotomy in the nature of pathogenic mutations associated with CBSDH. One group of mutations is classified as "pyridoxine-responsive," where CBS enzyme function may be partially restored by high dose Vitamin $B_6$ therapy. This treatment can be effective, but does not always mitigate the pathological events in these individuals, and some of the events occur even in these individuals over time. In a clinical setting "Vitamin B6 responsive" is defined as a 30% relative drop in Hcy that occurs 24 hours after an individual is given an oral dose of 100-500 mg of B6, meaning that a B6 responsive individual may still have abnormally high homocysteine levels. The second group of functional mutations is represented by the "C-terminal CBS mutants" that are defective in their ability to respond to post-translational up-regulation by S-adenosylmethionine. Individuals with this class of mutations usually lack the mental retardation and connective tissue aspects of the phenotype. This class is detected after measurement of plasma Hcy levels following an idiopathic thrombotic event before the age of 40 years (Maclean et al., 2002, *Hum. Mutat.* 19:641-55). The final group of CBSDH mutations is "classical homocystinuria," which represents the most severe form of the disease. For these latter two groups of individuals Vitamin B6 therapy in isolation does not effectively lower serum Hcy levels. These mutational groups may show phenotypic distinctions, but can be treated similarly.

The most common mutated CBS allele is 833T>C (I278T), which is associated with pyridoxine-responsive homocystinuria. Thus, $B_6$ responsive individuals account for approximately half of the homocystinuric patient population (Barber and Spaeth, 1969; Mudd et al., 1985). Of these $B_6$ responsive individuals, however, many are only partial responders, and in combination with $B_6$ non-responsive individuals, there arises a need for additional therapeutic options. Unfortunately, such therapeutic options are currently limited to reducing intake of methionine by following a strict low protein diet with supplemented cysteine (now essential) and decreasing homocysteine concentration via the use of betaine (N,N,N-trimethylglycine), a methyl donor able to re-methylate homocysteine back to methionine. Therefore, enzyme replacement therapy (ERT) using CBS (e.g., PEGylated htCBS described herein) may be the best therapy for both the $B_6$ partial and non-responsive patients.

As a result of CBS dysfunction, homocysteine (Hcy) levels are dramatically altered in CBSDH patients. In healthy individuals, total Hcy levels are in the range of ~5-15 µM (Stabler et al., 2002, Metabolism, 51:981-988), 98% of which is in the form of disulfides or is protein-bound. Only 2% of the tHcy exists as a free (non-protein-bound) reduced homocysteine, which can serve as a substrate for CBS (Mansoor et al., 1992, Anal. Biochem. 200:218-229; Mudd et al., 2000, Arterioscler. Thromb. Vasc. Biol. 20:1704-1706). This balance is dramatically altered in CBSDH patients, with free reduced homocysteine reaching 10-25% of tHcy values that are observed in these patients (up to ~400 µM) (Mansoor et al., 1993, Metabolism, 42:1481-1485).

Higher tHcy levels (e.g., greater than 54 times the wild type levels) may also cause diseases, disorders and/or conditions such as, but not limited to, facial alopecia, osteoporosis and reduction in mean survival. As a non-limiting example, model mice having at least 54 times higher tHcy as compared to wild type demonstrated several diseases, disorders and/or conditions, including facial alopecia, osteoporosis and reduction in mean survival. However, no such signs were observed in mice which had tHcy levels of about 30 times the normal values and thus homocysteine elevation may only pathogenic only above a threshold level (Gupta et al., 2009, FASEB J. 23:883-893). In a multicenter observational study of CBSDH in humans, it was found that even though various treatment combinations failed to restore normal homocysteine levels in CBSDH patients, and $B_6$ non-responders continued to exhibit homocysteine levels 3-5 times higher than the upper limit in the normal population, the risk of thromboembolism in these patients was significantly reduced (Yap et al., 2001, Arterioscler. Thromb. Vasc. Biol. 21, 2080-2085). Collectively, these data indicate that in order to ameliorate the clinical manifestation of CBSDH, an incomplete reduction of tHcy, as long as it is below a threshold level, may be sufficient to treat disease.

While a low methionine diet can be effective in establishing and maintaining some metabolic control of homocysteine levels in patients, its effect may be hindered by lack of dietary compliance especially in late-diagnosed patients, resulting in a concomitant increase in homocysteine accompanied by development of symptoms, especially in children (Walter et al., 1998, Eur. J. Pediatr. 157 Suppl 2, S71-76). Failure of dietary compliance causes increased serum Hcy, resurgence of complications in the vascular and connective tissue including fatal and incapacitating events, and risk of severe side-effects such as cerebral edema (from excessive serum Met concentration) or severe malnutrition (from lack of essential amino acids). The most effective therapeutic strategy is to increase enzyme activity, as is evident when given pyridoxine to Vitamin $B_6$ responsive homocystinuria. This strategy is not possible for Vitamin $B_6$ non-responsive individuals due to the mutation status. Betaine may help to achieve a metabolic control in less compliant patients and its combination with the diet may represent the best available treatment. However, current therapies for $B_6$ non-responders do not increase cystathionine, and cysteine supplementation may be warranted in order to maintain proper levels. Increased enzyme activity in these individuals may therefore depend on the delivery of exogenous enzyme, i.e. enzyme replacement therapy (ERT).

Considerable evidence suggests a possible function for cystathionine independent of its role as an intermediate in transsulfuration. A positive role for cystathionine has been suggested by studies of a particular transgenic mouse model of CBS-deficient homocystinuria. In this model of classical homocystinuria, the mouse cbs gene is inactivated and survives on low-level expression of the human CBS transgene under the control of the human CBS promoter; thus, it has been designated as "human only" (HO). The HO mouse exhibits severe elevations in both plasma and tissue levels of Hcy, methionine, S-adenosylmethionine, and S-adenosylhomocysteine and a concomitant decrease in plasma and hepatic levels of cysteine. However, in contrast to previous CBS knockout models of classical homocystinuria (also known as CBS knockout mice (KO) which suffer a severe growth retardation and hepatopathy and most die within three weeks after birth, even while mothers are on betaine (Maclean et al., 2010b. Mol. Genet. Metab. 101, 153-162)), which suffer severe growth retardation and hepatopathy, incur hepatic steatosis, fibrosis, and neonatal death within three weeks after birth even while mothers are treated with betaine, the HO mice exhibit mild hepatopathy and approximately 90% of HO mice live for at least 6 months (Maclean et al., 2012, J. Biol. Chem. 287, 31994-32005, the contents of which are herein incorporated by reference in its entirety). Tail bleeding determinations indicate that HO mice are in a hypercoagulative state that is significantly ameliorated by betaine treatment in a manner that recapitulates the disease as it occurs in humans (Maclean et al., 2010b. Mol. Genet. Metab. 101, 153-162; the contents of which are herein incorporated by reference in its entirety). HO mice have high levels of tHcy, but suffer only minor consequences. There is little or no difference in metabolite levels between these two murine models, except the level of cystathionine, which is significantly elevated in HO mice (~10 µM) as compared to KOs (~1 µM). Thus, it has been suggested that cystathionine may exert protective effects against hepatic and renal lipid accumulation, tissue injury and apoptotic cell death induced by prolonged endoplasmic reticulum stress.

Cystathionine may exert protective effects in a mouse model of acetaminophen-induced liver injury by serving as a cysteine prodrug. The use of the CGL inactivating compound D,1-2-amino-4-pentynoic acid in experiments to induce hypercystathionemia by blocking the conversion of cystathionine to cysteine coupled with the observation that cystathionine exerts significant protective effects in a23 cells that are incapable of converting this compound to cysteine, indicate that the protective effects observed are not a result of cystathionine acting as a precursor for cysteine synthesis.

Cystathionine may be important to the normally functioning brain. It is possible that cystathionine specifically accumulates in the normal mammalian brain to serve as a cytoprotectant and that the abolition of its synthesis could contribute to mental retardation in homocystinuria by increasing sensitivity of neural tissues to the toxic insult of elevated Hcy and/or derivatives thereof (Maclean et al., 2012, J. Biol. Chem. 287, 31994-32005). There are considerable regional differences in concentrations of cystathionine within the brain, and there is a higher concentration in white matter than in grey matter, suggesting a possible role in myelination. Cystathionine has been found in higher levels in occipital lobes of human and monkey brains than in the whole brain of lower animal species, and the role of cystathionine has been suggested to be more important in primate than in rodent brain (Volpe and Laster, 1972, *Biol. Neonate* 20, 385-403; the contents of which are herein incorporated by reference in its entirety).

A number of indirect lines of evidence support possible physiological roles for either cystathionine or a derivative thereof. In primate brain and central nervous system (CNS), there appears to be an imbalance between the relative activity levels of CBS and CGL leading to an accumulation of cystathionine. Similarly, during embryonic development, CBS is expressed in multiple tissues such as the heart and lungs that do not express any detectable CBS in adult tissues. A range of data indicates that CGL is not expressed during early mammalian development. In human liver samples for instance, CGL activity is only detected in post-natal tissue whereas activity in fetal, premature and full-term neonatal liver tissue is essentially undetectable. Collectively, these results indicate that at certain stages of development and in adult neural tissues, CBS is expressed specifically for the production of cystathionine distinct from its role as an intermediate in cysteine synthesis (Maclean et al., 2012, *J Biol. Chem.* 287, 31994-32005; the contents of which are herein incorporated by reference in its entirety). Taken with the knowledge that rigorous control over cystathionine γ-lyase (CGL) and CBS expression occurs during mammalian development, these observations come together to suggest a possible protective role for cystathionine in addition to being a precursor to cysteine.

Cysteine biosynthesis from cystathionine is catalyzed by CGL. Cystathionine is present inside the cells, and it is believed to not exist as a plasma protein. Accordingly, it is believed that the cystathionine produced upon injection of the PEGylated human truncated (htCBS) enzyme described herein may also serve as an intracellular substrate for CGL. Additionally, it may be possible that reduced levels of tHcy may impede the formation of cysteine-homocysteine adducts (which can be rapidly cleared in urine), generating higher levels of free cysteine in plasma (Gupta et al., 2014, *FASEB J.* 28:781-790).

Various aspects of the present invention now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

The CBS Enzyme

The CBS gene resides on human chromosome 21 at q22.3 (Skovby et al., *Hum. Genet.* 65:291-294 (1984); Munke et al., *Am. J. Hum. Genet.* 42:550-559 (1988); the contents of which are herein incorporated by reference in their entirety). The nucleic acid sequence encoding human CBS and the amino acid sequence encoded thereby are available through GenBank Accession No. L19501, and these sequences are also disclosed in U.S. Pat. No. 5,523,225, which is incorporated herein by reference in its entirety. The nucleic acid sequence of the genomic DNA encoding CBS is also publicly available through sequence databases such as GenBank and at University of Colorado-Denver webpage (Kraus Laboratory).

While not wishing to be bound by theory, the protein encoded by the CBS gene acts as a homotetramer to catalyze the conversion of homocysteine to cystathionine, the first step in the transsulfuration pathway. The encoded protein is allosterically activated by S-adenosyl-methionine and uses pyridoxal phosphate as a cofactor. Multiple alternatively spliced transcript variants have been found for this gene.

CBS governs the unidirectional flow of sulfur from methionine to cysteine by operating at the intersection of the transmethylation, transsulfuration and re-methylation pathways. It catalyzes a β-replacement reaction in which serine condenses with homocysteine in a pyridoxal 5'-phosphate (PLP)-dependent manner, to form cystathionine (Miles and Kraus, 2004, *J. Biol. Chem.* 279:29871-29874; the contents of which are herein incorporated by reference in its entirety). Cystathionine can then be converted to cysteine by Cystathionine Gamma Lyase (CGL). Thus, proper function of the CBS enzyme is critical for the regulation of both cysteine and methionine metabolism (Mudd et al., 2001, "Disorders of Transsulfuration." In The Metabolic and molecular bases of inherited disease. C. R. Scriver, A. L. Beudet, W. S. Sly, V. D., C. B., K. K. W., and V. B., eds. (New York: McGraw-Hill), pp. 2007-2056; the contents of which are herein incorporated by reference in its entirety), and accordingly, a compromised CBS activity or lack thereof, leads to the biochemical and clinical manifestations of CBS-deficient homocystinuria (CBSDH).

Inactivation of CBS results in cystathionine beta-synthase-deficient homocystinuria (CBSDH), more commonly referred to as classical homocystinuria. Classical homocystinuria was first described by Carson and Neill in 1962 (Carson and Neill, 1962. *Arch. Dis. Child* 37:505-513; the contents of which are herein incorporated by reference in its entirety) and is recognized as the most common inborn error of sulfur amino acid metabolism. The underlying cause of homocystinuria, a deficiency of the Cystathionine β-Synthase (CBS) enzyme, was discovered shortly thereafter (Mudd et al., 1964, *Science* 143:1443-1445; the contents of which are herein incorporated by reference in its entirety).

Missense mutations represent the most common cause of cystathionine β-synthase (CBS) deficiency. Many of these mutations result in misfolded proteins, which lack biological function. The presence of chemical chaperones (e.g., such as ethanol, dimethyl sulfoxide, or trimethylamine-N-oxide) can sometimes alleviate or even restore protein folding and activity of mutant proteins. Eight CBS mutant enzymes (P49L, P78R, A114V, R125Q, E176K, P422L, I435T, and S466L) were purified and characterized, and could be rescued with chemical chaperones by improving their protein folding. The tetrameric mutant enzymes fully saturated with heme had the same or higher specific activities than wild type CBS. Thermal stability measurements demonstrated that the purified mutants are equally or more thermostable than wild type CBS. The response to S-adenosyl-L-methionine stimulation or thermal activation varied. The lack of response of R125Q and E176K to both stimuli indicated that their specific conformations were unable to reach the activated state. Increased levels of molecular chaperones in crude extracts, particularly DnaJ, indicated a rather indirect effect of the chemical chaperones on folding of CBS mutants (Majtan, et al., 2010, *J. Biol. Chem.* 285(21): 15866-15873; the contents of which are herein incorporated by reference in its entirety).

The extent of misfolding of 27 CBS mutations previously tested in *E. coli* have been tested for the ability of chaperones to rescue the conformation of these mutations under the more folding-permissive conditions of mammalian CHO-K1 cells. Expression of mutations in mammalian cells increased the median activity 16-fold and the amount of tetramers 3.2-fold compared with expression in bacteria. Subsequently, the responses of seven selected mutations to three compounds with chaperone-like activity were tested. Aminooxyacetic acid and 4-phenylbutyric acid exhibited only a weak effect. In contrast, heme arginate substantially increased the formation of mutant CBS protein tetramers (up to sixfold) and rescued catalytic activity (up to ninefold) of five out of seven mutations (p.A114V, p.K102N, p.R125Q, p.R266K, and p.R369C). The greatest effect of heme arginate was observed for the mutation p.R125Q, which is non-responsive to in vivo treatment with vitamin B6. Moreover, the heme responsiveness of the p.R125Q mutation was confirmed in fibroblasts derived from a patient homozygous for this genetic variant. Based on these data, a distinct group of heme-responsive CBS mutations was proposed and the heme pocket of CBS was predicted to be an important target for designing novel therapies for homocystinuria (Melenovska, et al., 2014, *J. Inherit. Metab. Dis.* 38(2); the contents of which are herein incorporated by reference in its entirety).

Biochemically, CBSDH is characterized by highly elevated blood levels of homocysteine, methionine and S-adenosyl-homocysteine (also known as "SAH" or "AdoHcy"), accompanied by low levels of cysteine and cystathionine. Some of the clinical manifestations of untreated homocystinuria include thromboembolism, connective tissue problems such as dislocation of the optic lens, marfanoid features and osteoporosis, cognitive impairment and other signs (Kraus, J., and Kozich, V. (2001). "Cystathionine beta-synthase and its deficiency." In Homocysteine in health and disease. J. D. Carmel R, ed. (New York: Cambridge University Press), pp. 223-243; Mudd et al., 2001, "Disorders of Transsulfuration." In The Metabolic and molecular bases of inherited disease. C. R. Scriver, A. L. Beudet, W. S. Sly, V. D., C. B., K. K. W., and V. B., eds. (New York: McGraw-Hill), pp. 2007-2056).

Initial attempts to treat homocystinuria employed dietary restrictions to decrease the methionine intake, thus avoiding the build-up of the toxic homocysteine (Komrower et al., 1966, *Arch. Dis. Child* 41:666-671). It was later found that supplementation with the PLP-cofactor precursor, pyridoxine (vitamin $B_6$), relieves the clinical manifestations for slightly less than half of patients, and a subset of these are only partial responders (Barber and Spaeth, 1969. *J. Pediatr.* 75:463-478; Mudd et al., 1985, *Am. J. Hum. Genet.* 37:1-31). The "$B_6$ responders" need to take supplemental vitamin $B_6$ for the rest of their lives. In many cases, even full $B_6$-responsive patients require a milder protein restricted diet to be able to achieve a metabolic control (Picker, J. D., and Levy, H. L. (2004). Homocystinuria Caused by Cystathionine Beta-Synthase Deficiency. In GeneReviews. R. A. Pagon, M. P. Adam, T. D. Bird, C. R. Dolan, C. T. Fong, and K. Stephens, eds. (Seattle (Wash.): University of Washington, Seattle; the contents of each of which are herein incorporated by reference in their entirety). The remaining subset, the non-responders, are subjected to an extremely limited diet, with which many patients poorly comply (Walter et al., 1998, Eur. J. Pediatr. 157 Suppl 2, S71-76; the contents of which are herein incorporated by reference in its entirety). The diet is combined with a methionine-free and cysteine enriched amino acid mixture along with betaine, which can serve as a methyl donor for the enzyme betaine-homocysteine methyltransferase (BHMT) to produce dimethylglycine and methionine from homocysteine (Finkelstein, 1990, *J. Nutr. Biochem.* 1:228-237). Glutathione is synthesized from cysteine, and thus the addition of cysteine can be important to reduce oxidative stress. Most patients are also treated with trimethylglycine, and a normal dose of folic acid supplement. This improves the metabolic control by lowering homocysteine levels, in conjunction with the strict diet.

Betaine (N,N,N-trimethylglycine) is used to reduce concentrations of homocysteine by promoting the conversion of homocysteine back to methionine, i.e., increasing flux through the remethylation pathway independent of folate derivatives (which is mainly active in the liver and in the kidneys). A small portion of the re-formed methionine is then gradually removed by incorporation into body protein. The methionine that is not converted into protein is converted to S-adenosyl-methionine which goes on to form homocysteine again. Betaine is, therefore, most effective if the quantity of methionine to be removed is small. Hence treatment includes both betaine and a diet low in methionine. In classical homocystinuria, the plasma methionine level usually increases above the normal range of 30 micromoles/L and the concentrations should be monitored as potentially toxic levels (more than 400 micromoles/L) may be reached.

An alternative treatment strategy for CBSDH has long been sought to provide the $B_6$ non-responders and partial responders with a therapy that improves the metabolic abnormalities, reduces the accumulation of toxic homocysteine in circulation, and increases the levels of cystathionine and cysteine. Such metabolic changes may reverse, or delay, the onset of CBSDH symptoms, and allow this group of affected individuals to enjoy an unrestricted or only mildly restricted diet and significantly improve their quality of life. To provide these benefits, a therapy must improve the core deficiency that underlies this condition, namely, aberrant CBS levels and/or function. Accordingly, systemic introduction of CBS, in the form of Enzyme Replacement Therapy (ERT), should be beneficial for homocystinuric patients.

Without being bound by theory, a significant decrease in extracellular homocysteine due to CBS administration is believed to generate a concentration gradient, triggering a flux of homocysteine from intra- to extra-cellular spaces, where the administered enzyme can further process it, and thus the extracellular CBS can serve as a homocysteine "sink."

The structure and mode of activation of native human CBS, which exists as a tetramer, comprised of four identical monomers may be difficult to use as ERT. This form of the enzyme has a high tendency for aggregation, which poses a major constraint on the purification efforts (Kraus and Rosenberg, 1983, *Arch. Biochem. Biophys.* 222:44-52; the contents of which are herein incorporated by reference in its entirety). Additionally, CBS activation requires the binding of S-Adenosyl-methionine (SAM) to the C-terminal tail, in order to relieve the auto-inhibition exerted on the enzyme by its C-terminal regulatory region.

A truncated recombinant human CBS (htCBS) is provided (SEQ ID NO: 3) where the C-terminal regulatory region has been removed. In one embodiment, the htCBS may be mutated where cysteine at amino acid position 15 has been changed to serine (htCBS mutant or C15S) (SEQ ID NO: 13).

In one embodiment, PEGylated htCBS or PEGylated htCBS mutant enzyme improved the pharmacokinetic and pharmacodynamic properties of the enzyme in vivo. Therapeutic proteins, unlike small molecules, are delivered via parenteral routes, and treatment efficacy may be greatly impacted by their absorption, distribution, metabolism and excretion ("ADME") (Vugmeyster et al., 2012, *World Journal of Biological Chemistry* 3:73-92; the contents of which are herein incorporated by reference in its entirety). High molecular weight compounds, such as enzymes, have limited tissue penetration capability, and are thus mainly present in the plasma until they are removed from circulation by at least one mechanism.

In one embodiment, administration of htCBS or htCBS mutant for ERT maintains high activity in plasma for a period of time that is sufficient to deliver a steady and significant effect on sulfur amino acid metabolism. Enhancing ERT efficacy may require additional modifications to the protein, in order to increase retention time in vivo. This may be achieved by PEGylation, the addition of Poly-Ethylene-Glycol (PEG) moieties onto the surface of the protein, in order to extend the retention time in a subject. PEGylation was found to minimize proteolysis, immune response and antigenicity, while increasing protein stability and size, and reducing renal excretion (Kang et al., 2009, *Expert opinion on emerging drugs* 14:363-380; the contents of which are herein incorporated by reference in its entirety).

Cysteine biosynthesis from cystathionine is catalyzed solely by CGL. Cystathionine is only present inside the cells, and does not exist as a plasma protein. Accordingly, it is believed that the cystathionine produced upon injection of the PEGylated htCBS or PEGylated htCBS mutant enzyme described herein may also serve as an intracellular substrate for CGL. Additionally, and not mutually exclusively, it is also possible that reduced levels of tHcy may impede the formation of cysteine-homocysteine adducts (which can be rapidly cleared in urine), generating higher levels of free cysteine in plasma, as was recently suggested (Gupta et al., 2014, *FASEB J.* 28, 781-790). Normalizing cysteine levels without cysteine supplementation is another potential advantage of the presently described htCBS and htCBS mutant in ERT.

In one embodiment, normalization of cysteine levels may be observed following administration of the PEGylated htCBS or PEGylated htCBS mutant enzyme. In addition to a change in metabolite levels, another positive effect of htCBS or htCBS mutant administration may be predicted to be a significant impact on liver disease and survival of affected CBSDH patients.

Methods of Using PEGylated htCBS

In one embodiment, the compositions and methods described herein may be used to treat CBSDH. There are three groups of pathogenic mutations associated with CBSDH, (1) pyridoxine-responsive mutations, (2) C-terminal CBS mutants and (3) classical homocystinuria.

In one embodiment, htCBS and htCBS mutant enzyme replacement may be used to treat CBSDH. The htCBS and htCBS mutant enzyme may be PEGylated by a method known in the art or described herein. As a non-limiting example, the PEG may be a low molecular weight (e.g., 2 kDa) PEG or a high molecular weight (e.g., 40 kDa) four arm branched PEG.

In one embodiment, PEGylated htCBS or PEGylated htCBS mutant and methods of using the PEGylated htCBS or PEGylated htCBS mutant described herein may be used to treat subjects with pyridoxine-responsive mutations. PEGylated htCBS or PEGylated htCBS mutant may be used alone or in combination with current therapies (e.g., Vitamin B6 or Betaine) to treat subjects with pyridoxine-responsive mutations. As a non-limiting example, the PEGylated htCBS or PEGylated htCBS mutant may be used to mitigate or reduce pathological events in subjects with pyridoxine-responsive mutations. As a non-limiting example, the PEGylated htCBS or PEGylated htCBS mutant may be used to treat a subject with pyridoxine-responsive mutations who is a partial responder to Vitamin B6 therapy. As another non-limiting example, the PEGylated htCBS or PEGylated htCBS mutant may be used to treat a subject with pyridoxine-responsive mutations who is a non-responder to Vitamin B6 therapy.

In one embodiment, PEGylated htCBS or PEGylated htCBS mutant and methods of using the PEGylated htCBS or PEGylated htCBS mutant described herein may be used to treat subjects with C-terminal CBS mutations. PEGylated htCBS or PEGylated htCBS mutant may be used alone or in combination with current therapies (e.g., Vitamin B6 or Betaine) to treat subjects with C-terminal CBS mutations. As a non-limiting example, the PEGylated htCBS or PEGylated htCBS mutant may be used to lower serum Hcy levels in subjects with C-terminal CBS mutations. As a non-limiting example, the PEGylated htCBS or PEGylated htCBS mutant may be used to treat a subject with C-terminal CBS mutations who is a partial responder to Vitamin B6 therapy. As another non-limiting example, the PEGylated htCBS or PEGylated htCBS mutant may be used to treat a subject with C-terminal CBS mutations who is a non-responder to Vitamin B6 therapy.

In one embodiment, PEGylated htCBS or PEGylated htCBS mutant and methods of using the PEGylated htCBS or PEGylated htCBS mutant described herein may be used to treat subjects with classical homocystinuria. PEGylated htCBS or PEGylated htCBS mutant may be used alone or in combination with current therapies (e.g., Vitamin B6 or Betaine) to treat subjects with classical homocystinuria. As a non-limiting example, the PEGylated htCBS or PEGylated htCBS mutant may be used to lower serum Hcy levels in subjects with classical homocystinuria. As a non-limiting example, the PEGylated htCBS or PEGylated htCBS mutant may be used to treat a subject with classical homocystinuria who is a partial responder to Vitamin B6 therapy. As another non-limiting example, the PEGylated htCBS or PEGylated htCBS mutant may be used to treat a subject with classical homocystinuria who is a non-responder to Vitamin B6 therapy.

In one embodiment, the compositions and methods described herein may be used to reduce a symptom, disease or disorder associated with CBSDH. The symptom, disease or disorder may be in an organ system or a severe phenotypic change. Non-limiting examples of diseases, disorders and/or conditions from CBSDH include mental retardation, psychiatric disturbances, central nervous system problems including seizures, cardiovascular disease with a predisposition to thromboembolic complications resulting in a high rate of mortality in untreated and partially treated individuals, and a range of connective tissue disorders affecting the ocular system (e.g., progressive myopia and lens dislocation, ectopia lentis), and skeletal system (e.g., marfanoid habitus, osteoporosis, scoliosis, fine fair hair and brittle, thin skin).

In one embodiment, the compositions and methods described herein may be used to treat a disease, disorder and/or condition such as, but not limited to, thromboembolism, connective tissue problems such as dislocation of the optic lens, marfanoid features, osteoporosis, and cognitive impairment.

In one embodiment, the PEGylated htCBS or PEGylated htCBS mutant enzyme described herein may reduce the effects and/or treat liver disease. The liver disease may be in a subject with CBSDH. The treatment and/or reduction of the effects of liver disease may thus increase the rate of survival of CBSDH patients. As a non-limiting example, PEGylated htCBS or PEGylated htCBS mutant may be used to reduce liver parenchyma damage.

In one embodiment, PEGylated htCBS or PEGylated htCBS mutant may be used to increase cystathionine and treat or reduce the effects of liver disease or injury.

In one embodiment, the compositions and methods described herein (e.g., enzyme replacement therapy (ERT)) using the PEGylated htCBS or PEGylated htCBS mutant enzyme can ameliorate the disease manifestations and metabolic abnormalities that characterize the homocystinuria.

In one embodiment, ERT using PEGylated htCBS or PEGylated htCBS mutant enzyme offers an effective therapy for CBSDH patients to allow prevention and treatment of and/or amelioration of symptoms of homocystinuria, and relieving the need to maintain such a strict protein-excluding diet.

In one embodiment, PEGylated htCBS or PEGylated htCBS mutant may be used to increase cystathionine and treat or reduce the effects of mental retardation in homocystinuria subjects. The amount of cystathionine may be increased in a region or area of the brain such as, but not limited to, occipital lobes grey matter and white matter.

In one embodiment, PEGylated htCBS or PEGylated htCBS mutant may be used to increase sensitivity of neural tissues in the brain of homocystinuria subjects. The amount of cystathionine may be increased in a region or area of the brain such as, but not limited to, occipital lobes grey matter and white matter.

In one embodiment, PEGylated htCBS or PEGylated htCBS mutant may be used to extend the life of a subject with CBSDH.

In one embodiment, PEGylated htCBS or PEGylated htCBS mutant is used as part of CBS enzyme replacement therapy (ERT) for the treatment of homocystinuria. The administration of PEGylated htCBS and htCBS mutant may not necessitate introduction of the deficient enzyme into its natural intracellular compartment.

In one embodiment, administration of PEGylated htCBS or PEGylated htCBS mutant decrease homocysteine levels by 5%, 10%, 15%, 20%, 25%, 30%, 33%, 35%, 40%, 45%, 50%, 52%, 55%, 60%, 65%, 67%, 69%, 70%, 74%, 75%, 76%, 77%, 80%, 85%, 90%, 95% or more than 95%. As a non-limiting example, the decrease of homocysteine may be a decrease of about 69%. As a non-limiting example, the decrease of homocysteine may be a decrease of about 67%. As a non-limiting example, the decrease of homocysteine may be a decrease of about 52%. As a non-limiting example, the decrease of homocysteine may be a decrease of about 33%.

In one embodiment, PEGylated htCBS or PEGylated htCBS mutant may be administered before, after or concurrently with traditional betaine treatment. The combination therapy may result in synergistic effects on homocysteine levels.

In one embodiment, administration of PEGylated htCBS or PEGylated htCBS mutant to a subject may alter the extra- and intra-cellular equilibrium of sulfur amino acids.

In one embodiment, the alteration of extra- and intra-cellular equilibrium may be a decrease in the plasma homocysteine such as, but not limited to, a decrease of about 5%, 10%, 15%, 20%, 25%, 30%, 33%, 35%, 40%, 45%, 50%, 52%, 55%, 60%, 65%, 67%, 69%, 70%, 74%, 75%, 76%, 77%, 80%, 85%, 90%, 95% or more than 95%. As a non-limiting example, the decrease of plasma homocysteine may be a decrease of about 75%.

In one embodiment, the alteration of extra- and intra-cellular equilibrium may be an increase in cystathionine such as, but not limited to, an increase of about 10%, 20%, 30%, 40%, 50%, 60%, 70%, 80%, 90%, 100%, 110%, 1120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 410%, 420%, 430%, 440%, 450%, 460%, 470%, 480%, 490%, 500%, 510%, 520%, 530%, 540%, 550%, 560%, 570%, 580%, 590%, 600%, 610%, 620%, 630%, 640%, 650%, 660%, 670%, 680%, 690%, 700%, 710%, 720%, 730%, 740%, 750%, 760%, 770%, 780%, 790%, 800%, 810%, 820%, 830%, 840%, 850%, 860%, 870%, 880%, 890%, 900%, 910%, 920%, 930%, 940%, 950%, 960%, 970%, 980%, 990%, 1000% or more than 1000%. As a non-limiting example, increase in cystathionine may be about 900%.

In one embodiment, the alteration of extra- and intra-cellular equilibrium may be the normalization of cysteine concentrations that is reflected in improvement of histopathological changes in the liver and increased survival.

In one embodiment, PEGylated htCBS or PEGylated htCBS mutant may be used to reduce tHcv levels in a subject with CBSDH. The tHCV levels may be reduced to 1, 2, 3, 4, 5, 6, 7, 8, 9, 10, 11, 12, 13, 14, 15, 16, 17, 18, 19, 20 21, 22, 23, 24, 15, 26, 27, 28, 29, 30, 31, 32, 33, 34, 35, 36, 37, 38, 39, 40, 41, 42, 43, 44, 45, 46, 47, 48, 49, 50, 51, 52, 53, 54, 1-5, 1-10, 1-20, 1-30, 1-40, 1-50, 2-5, 2-10, 2-20, 2-30, 2-40, 2-50, 3-5, 3-10, 3-20, 3-30, 3-40, 3-50, 4-6, 4-10, 4-20, 4-30, 4-40, 4-50, 5-7, 5-10, 5-20, 5-30, 5-40, 5-50, 6-8, 6-10, 6-20, 6-30, 6-40, 6-50, 7-10, 7-20, 7-30, 7-40, 7-50, 8-10, 8-20, 8-30, 8-40, 8-50, 9-10, 9-20, 9-30, 9-40, 9-50, 10-20, 10-30, 10-40, 10-50, 20-30, 20-40, 20-50, 30-40, 30-50 or 40-50 times the wild type level. As a non-limiting example, the tHCY level is reduced to about 30 times the wild type level. As a non-limiting example, the tHCY level is reduced to about 3-5 times the wild type level.

In one embodiment PEGylated htCBS or PEGylated htCBS mutant may be used to lower tHcv levels and thus treat or reduce the effects of diseases, disorders and/or conditions associated with high tHCY levels (e.g., greater than 54 times the wild type level). Non-limiting examples, of diseases, disorder and/or conditions associated with high tHCY levels include facial alopecia, osteoporosis and reduction in mean survival.

In one embodiment, the PEGylated htCBS or PEGylated htCBS mutant described herein may be used to normalizing cysteine levels without cysteine supplementation.

In one embodiment, the PEGylated htCBS or PEGylated htCBS mutant described herein may be used in combination with Betaine to reduce concentrations of homocysteine in a subject. Homocysteine may be reduced about 5%, 10%, 15%, 20%, 25%, 30%, 33%, 35%, 40%, 45%, 50%, 52% 55%, 60%, 65%, 67%, 69%, 70%, 74%, 75%, 76%, 77%, 80%, 85%, 90%, 95% or more than 95% in a subject using the combination therapy. As a non-limiting example, homocysteine may be reduced 77%. As a non-limiting example, homocysteine may be reduced 76%. As a non-limiting example, homocysteine may be reduced 74%. As a non-limiting example, homocysteine may be reduced 40%.

In one embodiment, the PEGylated htCBS or PEGylated htCBS mutant described herein may be used to cause a change such as an increase and/or decrease in metabolite levels.

In one embodiment, the PEGylated htCBS or PEGylated htCBS mutant described herein may be used to cause a change such as an increase in metabolite levels. As a non-limiting example, the metabolite may be cystathionine and cysteine which may be increased 5%, 10%, 15%, 20%, 25%, 30%, 33%, 35%, 40%, 45%, 50%, 52% 55%, 60%, 65%, 67%, 69%, 70%, 74%, 75%, 76%, 77%, 80%, 85%, 90%, 95%, 100%, 110%, 1120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 410%, 420%, 430%, 440%, 450%, 460%, 470%, 480%, 490%, 500%, 510%, 520%, 530%, 540%, 550%, 560%, 570%, 580%, 590%, 600%, 610%, 620%, 630%, 640%, 650%, 660%, 670%, 680%, 690%, 700%, 710%, 720%, 730%, 740%, 750%, 760%, 770%, 780%, 790%, 800%, 810%, 820%, 830%, 840%, 850%, 860%, 870%, 880%, 890%, 900%, 910%, 920%, 930%, 940%, 950%, 960%, 970%, 980%, 990%, 1000% or more than 1000%. As a non-limiting example, the amount of cystathionine may be increased to be above 0.008, 0.01, 0.015, 0.020, 0.025, 0.03, 0.035, 0.04, 0.045, 0.05, 0.055, 0.06, 0.065, 0.07, 0.075, 0.08, 0.085, 0.09, 0.095, 0.1, 0.15, 0.2, 0.25, 0.3, or 0.35 uM or cystathionine may be increased to be between 0.05 and 0.35 uM. As another non-limiting example, the amount of cysteine may be increased to be above 140, 150, 160, 170, 180, 190, 200, 210, 220, 230, 240, 250, 260, 270, 280, 290, 300, 310, 320, 330, 340, 350, 360, 370, 380, 390, 400 or cysteine may be increased to be between 200 uM and 400 uM.

In one embodiment, the PEGylated htCBS or PEGylated htCBS mutant described herein may be used to cause a change such as a decrease in metabolite levels. As a non-limiting example, the metabolite may be homocysteine, methionine and S-adenosyl homocysteine which may be decreased by 5%, 10%, 15%, 20%, 25%, 30%, 33%, 35%, 40%, 45%, 50%, 52% 55%, 60%, 65%, 67%, 69%, 70%, 74%, 75%, 76%, 77%, 80%, 85%, 90%, 95%, 99% or 100%. As a non-limiting example, the amount of homocysteine may be decreased to be about 100, 95, 90, 85, 80, 75, 70, 65, 60, 55, 50, 45, 40, 35, 30, 25, 20, 15, 10, 5, 4, 3, 2 or 1 uM. As a non-limiting example, the amount of methionine may be decreased to be about 50, 45, 40, 35, 30, 25, 20, 15, 10, 5, 4, 3, 2 or 1 uM. As another non-limiting example, the amount of S-adenosyl homocysteine is decreased to be about 0.15, 0.14, 0.13, 0.12, 0.11, 0.10, 0.095, 0.09, 0.085, 0.08, 0.075, 0.07, 0.065, 0.06, 0.055, 0.05, 0.045, 0.04, 0.035, 0.03, 0.025, 0.02, 0.015, 0.01, 0.009, 0.008, 0.007, 0.006, 0.005, 0.004, 0.003, 0.002, 0.001 or less than 0.001 uM.

In one embodiment, the PEGylated htCBS or PEGylated htCBS mutant described herein may be used to reduce levels of homocysteine, methionine, S-adenosyl-methionine and S-adenosyl-homocysteine in a subject.

In one embodiment, the PEGylated htCBS or PEGylated htCBS mutant may be used to increase the levels of cysteine and cystathionine in a subject.

In a further aspect the present invention relates to a method to recombinantly produce and purify a human cystathionine synthase. The method includes the step of cloning a nucleic acid sequence encoding a human CBS enzyme or a truncated or mutated variant thereof into an expression vector. As a non-limiting example, the enzyme and method may be as set forth in International publication WO2014120770, the contents of which are herein incorporated by reference, and specifically as in SEQ ID NO: 01, SEQ ID NO: 02, SEQ ID NO: 3, SEQ ID NO: 4, SEQ ID NO: 13, SEQ ID NO: 14, SEQ ID NO: 15, and SEQ ID NO: 16.

Administration and Dosing

In one embodiment, PEGylated htCBS or PEGylated htCBS mutant may be administered to a subject by parenteral administration.

In one embodiment, PEGylated htCBS or PEGylated htCBS mutant may be administered to a subject by subcutaneous (SQ), intravenous (IV) or intraperitoneal (IP) injection. As a non-limiting example, PEGylated htCBS or PEGylated htCBS mutant may be administered to a subject by subcutaneous administration. As a non-limiting example, PEGylated htCBS or PEGylated htCBS mutant may be administered to a subject by intravenous administration. As a non-limiting example, PEGylated htCBS or PEGylated htCBS mutant may be administered to a subject by intraperitoneal administration.

In one embodiment, the PEGylated htCBS or PEGylated htCBS mutant may be administered to a subject at least 1, 2, 3, 4, 5, 6, 7, 8, 9, 10, 11, 12, 13, 14, 15, 16, 17, 18, 19, 20 or more than 20 times.

In one embodiment, the administration of the PEGylated htCBS or PEGylated htCBS mutant may be repeated every minute, 2 minutes, 3 minutes, 4 minutes, 5 minutes, six 6, 7 minutes, 8 minutes, 9 minutes, 10 minutes, 15 minutes, 20 minutes, 25 minutes, 30 minutes, 35 minutes, 40 minutes, 45 minutes, 50 minutes, 55 minutes, hourly, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, daily, 2 days, 3 days, 4 days, 5 days, 6 days, weekly, biweekly, 3 weeks, monthly, 2 months, quarterly, 4 months, 5 months, 6 months, 7 months, 8 months, 9 months, 10 months, 11 months, yearly, 13 months, 14 months, 15 months, 16 months, 17 months, or 18 months.

In one embodiment, the administration of the PEGylated htCBS or PEGylated htCBS mutant may be a series of doses which are minutes, hours, days or weeks apart. The number of doses in a series may be 2, 3, 4, 5 or 6. As a non-limiting example, a subject is administered 3 doses 24 hours apart. As another non-limiting example, a subject is administered 5 doses 12 hours apart.

In one embodiment, the administration of the PEGylated htCBS or PEGylated htCBS mutant may follow a dosing schedule of a series of doses that has a gap between the first series and the second series of doses. The gap between the doses may be 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, day, 2 days, 3 days, 4 days, 5 days, 6 days, week, 2 weeks, 3 weeks, monthly, 2 months, quarterly, 4 months, 5 months, 6 months, 7 months, 8 months, 9 months, 10 months, 11 months, 12 months, 13 months, 14 months, 15 months, 16 months, 17 months, or 18 months. The number of doses in a series may be 2, 3, 4, 5 or 6. As a non-limiting example, a subject may be administered a first series of 5 doses 12 hours apart and then 14 days after the first dose a subject is administered a second series of 5 doses 12 hours apart. As another non-limiting example, a subject is administered two series of doses over a period of 8 weeks where the first series is one dose twice a week for two weeks and the second series of doses is three times a week for 6 weeks.

In one embodiment, PEGylated htCBS or PEGylated htCBS mutant may be administered at least once after a subject has been administered Betaine. The time between the Betaine administration the PEGylated htCBS may be 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, day, 2 days, 3 days, 4 days, 5 days, 6 days, week, 2 weeks, 3 weeks, monthly, 2 months, quarterly, 4 months, 5 months, 6 months, 7 months, 8 months, 9 months, 10 months, 11 months, 12 months, 13 months, 14 months, 15 months, 16 months, 17 months, or 18 months. As a non-limiting example, the PEGylated htCBS may be administered 14 days after the subject was administered Betaine. As another non-limiting example, a subject may be administered two doses after the subject was administered Betaine. The PEGylated htCBS or PEGylated htCBS mutant may be administered 14 and 15 days after Betaine administration.

In one embodiment, PEGylated htCBS or PEGylated htCBS mutant may be administered in combination with Betaine to a subject. The combination may be administered at least 1, 2, 3, 4, 5, 6, 7, 8, 9, 10, 11, 12, 13, 14, 15 or more than 15 times.

In one embodiment, PEGylated htCBS or PEGylated htCBS mutant may be administered in combination with Betaine to a subject after the subject has initially received Betaine. The time between the combination treatment and the original Betaine administration may be 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, day, 2 days, 3 days, 4 days, 5 days, 6 days, week, 2 weeks, 3 weeks, monthly, 2 months, quarterly, 4 months, 5 months, 6 months, 7 months, 8 months, 9 months, 10 months, 11 months, 12 months, 13 months, 14 months, 15 months, 16 months, 17 months, or 18 months. As a non-limiting example, the combination may be administered 14 days after the subject was first administered Betaine. As another non-limiting example, a subject may be administered two doses after the subject was first administered Betaine. The combination may be administered 14 and 15 days after Betaine administration.

In one embodiment, the dose of PEGylated htCBS or PEGylated htCBS mutant administered to a subject may be between 5 and 8 mg/kg such as 5 mg/kg, 5.5 mg/kg, 6 mg/kg, 6.5 mg/kg, 7 mg/kg, 7.5 mg/kg or 8 mg/kg.

In one embodiment, the PEGylated htCBS or PEGylated htCBS mutant may be co-administered with another therapeutic for treating CBSDH. As used herein, "co-administered" means the administration of two or more components. These components for co-administration include, but are not limited to PEGylated htCBS, PEGylated htCBS mutant, betaine or Vitamin B6. Co-administration refers to the administration of two or more components simultaneously or with a time lapse between administration such as 1 second, 5 seconds, 10 seconds, 15 seconds, 30 seconds, 45 seconds, 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, 29 minutes, 30 minutes, 31 minutes, 32 minutes, 33 minutes, 34 minutes, 35 minutes, 36 minutes, 37 minutes, 38 minutes, 39 minutes, 40 minutes, 41 minutes, 42 minutes, 43 minutes, 44 minutes, 45 minutes, 46 minutes, 47 minutes, 48 minutes, 49 minutes, 50 minutes, 51 minutes, 52 minutes, 53 minutes, 54 minutes, 55 minutes, 56 minutes, 57 minutes, 58 minutes, 59 minutes, 1 hour, 1.5 hours, 2 hours, 2.5 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 1.5 days, 2 days, or more than 3 days.

Definitions

As used in this specification, the singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

Where a range of values is provided, it is intended that each intervening value between the upper and lower limit of that range and any other stated or intervening value in that stated range is encompassed within the disclosure and specifically disclosed. For example, if a range of 1 µm to 8 µm is stated, it is intended that 2 µm, 3 µm, 4 µm, 5 µm, 6 µm, and 7 µm are also explicitly disclosed, as well as the range of values greater than or equal to 1 µm and the range of values less than or equal to 8 µm.

"Coding sequence" refers to that portion of a nucleic acid (e.g., a gene) that encodes (i) an mRNA that is translated into an amino acid sequence of a protein; or (ii) a functional RNA, such as an interfering RNA or antisense molecule.

"Recombinant," when used with reference to, e.g., a cell, nucleic acid, polypeptide, expression cassette or vector, refers to a material, or a material corresponding to the natural or native form of the material, that has been modified by the introduction of a new moiety or alteration of an existing moiety, or is identical thereto but produced or derived from synthetic materials. For example, recombinant cells express genes that are not found within the native (non-recombinant) form of the cell (i.e., "exogenous nucleic acids") or express native genes that are otherwise expressed at a different level, typically, under-expressed or not expressed at all.

Recombinant techniques can include, e.g., use of a recombinant nucleic acid such as a cDNA encoding a protein or an antisense sequence, for insertion into an expression system, such as an expression vector; the resultant construct is introduced into a cell, and the cell expresses the nucleic acid, and the protein, if appropriate. Recombinant techniques also encompass the ligation of nucleic acids to coding or promoter sequences from different sources into one expression cassette or vector for expression of a fusion protein, constitutive expression of a protein, or inducible expression of a protein.

The terms "subject", "individual" or "patient" are used interchangeably herein and refer to a vertebrate, preferably a mammal. Mammals include, but are not limited to, humans.

"Associated" refers to coincidence with the development or manifestation of a disease, condition or phenotype. Association may be due to, but is not limited to, genes responsible for housekeeping functions whose alteration can provide the foundation for a variety of diseases and conditions, those that are part of a pathway that is involved in a specific disease, condition or phenotype and those that indirectly contribute to the manifestation of a disease, condition or phenotype.

"Physiological conditions" or "physiological solution" refers to an aqueous environment having an ionic strength, pH, and temperature substantially similar to conditions in an intact mammalian cell or in a tissue space or organ of a living mammal. Typically, physiological conditions comprise an aqueous solution having about 150 mM NaCl, pH 6.5-7.6, and a temperature of approximately 22-37 degrees C. Generally, physiological conditions are suitable binding conditions for intermolecular association of biological macromolecules. For example, physiological conditions of 150 mM NaCl, pH 7.4, at 37 degrees C. are generally suitable.

"Pharmaceutically acceptable excipient or carrier" refers to an excipient that may optionally be included in the compositions of the invention and that causes no significant adverse toxicological effects to the patient. In particular, in the present instance, such refers to an excipient that can be taken into the mammalian subject's body in association with an active compound (here PEGylated htCBS) with no significant adverse toxicological effects to the subject.

The term "excipient" or "vehicle" as used herein means any substance, not itself a therapeutic agent, used as a carrier for delivery of a therapeutic agent and suitable for administration to a subject, e.g. a mammal or added to a pharmaceutical composition to improve its handling or storage properties or to permit or facilitate formation of a dose unit of the composition into a discrete article such as a capsule or tablet suitable for oral administration. Excipients and vehicles include any such materials known in the art, e.g., any liquid, gel, solvent, liquid diluent, solubilizer, or the like, which is nontoxic and which does not interact with other components of the composition in a deleterious manner. Administration can mean oral administration, inhalation, enteral administration, feeding or inoculation by intravenous injection. The excipients may include standard pharmaceutical excipients, and may also include any components that may be used to prepare foods and beverages for human and/or animal consumption, feed or bait formulations or other foodstuffs.

"Permeant," "drug," or "pharmacologically active agent" or any other similar term means any chemical or biological material or compound, inclusive of peptides, suitable for administration by the methods previously known in the art and/or by the methods taught in the present disclosure, that induces a desired biological or pharmacological effect, which may include, but is not limited to (1) having a prophylactic effect on the organism and preventing an undesired biological effect such as preventing an infection, (2) alleviating a condition caused by a disease, for example, alleviating pain or inflammation caused as a result of disease, and/or (3) either alleviating, reducing, or completely eliminating the disease from the organism. The effect may be local, such as providing for a local anaesthetic effect, or it may be systemic. This disclosure is not drawn to novel permeants or to new classes of active agents. Rather it is limited to the mode of delivery of agents or permeants which exist in the state of the art or which may later be established as active agents and which are suitable for delivery by the present disclosure.

The term "about," particularly in reference to a given quantity, is meant to encompass deviations of plus or minus five percent.

"Optional" or "optionally" means that the subsequently described circumstance may or may not be present or occur, so that the description includes instances where the circumstance is present or occurs and instances where it is not present or does not occur.

"Substantially absent" or "substantially free" of a certain feature or entity means nearly totally or completely absent the feature or entity. For example, for a subject administered PEGylated htCBS, the substantial absence of an observable side effect means that such side effect is either non-detectable, or occurs only to a negligible degree, e.g., to an extent or frequency that is reduced by about 50% or more when compared to either the frequency or intensity of the same side effect observed in an untreated patient.

The terms "pharmacologically effective amount" or "therapeutically effective amount" as related to the present composition refer to a non-toxic, but sufficient amount of the active agent (or composition containing the active agent) to provide the desired level in the bloodstream or at the site of action (e.g. intracellularly) in the subject to be treated, and/or to provide a desired physiological, biophysical, biochemical, pharmacological or therapeutic response, such as amelioration of the manifestations of homocystinuria. The exact amount required will vary from subject to subject, and will depend on numerous factors, such as the active agent, the activity of the composition, the delivery device employed, the physical characteristics of the composition, intended patient use (i.e., the number of doses administered per day), as well as patient considerations, such as species, age, and general condition of the subject, the severity of the condition being treated, additional drugs being taken by the subject, mode of administration, and the like. These factors and considerations can readily be determined by one skilled in the art, based upon the information provided herein. An appropriate "effective" amount in any individual case may be determined by one of ordinary skill in the art using routine experimentation, based upon the information provided herein.

The term "biological activity" refers to any biological activity typically attributed to a nucleic acid or protein by those skilled in the art. Examples of biological activities are enzymatic activity, ability to dimerize, fold or bind another protein or nucleic acid molecule, etc.

The term "nucleic acid" may be in the form of RNA or in the form of DNA, and include messenger RNA, synthetic RNA and DNA, cDNA, and genomic DNA. The DNA may be double-stranded or single-stranded, and if single-stranded may be the coding strand or the non-coding (anti-sense, complementary) strand.

As used herein, a "variant" is a nucleic acid, protein or polypeptide which is not identical to, but has significant homology (for example, 80%, 85%, 90%, 91%, 92%, 93%, 94%, 95%, 96%, 97%, 98% or 99% sequence identity) over the entire length of the wild type nucleic acid or amino acid sequence, as exemplified by sequences in the public sequence databases, such as GenBank. As used herein, a "protein, polypeptide or peptide fragment thereof" means the full-length protein or a portion of it having an amino acid sequence usually at least 5, 6, 7, 8, 9, 10, 11, 12, 13, 14 or 15 amino acids in length, although dipeptides, tripeptides and tetrapeptides are also contemplated and encompassed by the present disclosure.

As used herein, a "mutant" is a mutated protein designed or engineered to alter properties or functions relating to glycosylation, protein stabilization and/or ligand binding.

As used herein, the terms "native" or "wild-type" relative to a given cell, polypeptide, nucleic acid, trait or phenotype, refers to the form in which that is typically found in nature.

As used herein, the terms "protein," "polypeptide," "oligopeptide" and "peptide" have their conventional meaning and are used interchangeably to denote a polymer of at least two amino acids covalently linked by an amide bond, regardless of length or post-translational modification (e.g., glycosylation, phosphorylation, lipidation, myristilation, ubiquitination, etc.). Furthermore, the polypeptides described herein are not limited to a specific length. Included within this definition are D- and L-amino acids, and mixtures of D- and L-amino acids. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Polypeptides can also refer to amino acid subsequences comprising epitopes, i.e., antigenic determinants substantially responsible for the immunogenic properties of a polypeptide and being capable of evoking an immune response.

"Position corresponding to" refers to a position of interest (i.e., base number or residue number) in a nucleic acid molecule or protein relative to the position in another reference nucleic acid molecule or protein. Corresponding positions can be determined by comparing and aligning sequences to maximize the number of matching nucleotides or residues, for example, such that identity between the sequences is greater than 90%, greater than 95%, greater than 96%, greater than 97%, greater than 98% or greater than 99%. The position of interest is then given the number assigned in the reference nucleic acid molecule. For example, if a particular polymorphism in Gene-X occurs at nucleotide 2073 of SEQ ID No. X, to identify the corresponding nucleotide in another allele or isolate, the sequences are aligned and then the position that lines up with 2073 is identified. Since various alleles may be of different length, the position designate 2073 may not be nucleotide 2073, but instead is at a position that "corresponds" to the position in the reference sequence.

"Percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)). Examples of algorithms that are suitable for determining percent sequence identity and sequence similarity are the BLAST and BLAST 2.0 algorithms, which are described in Altschul et al. (1990) *J Mol. Biol.* 215: 403-410 and Altschul et al. (1977) *Nucleic Acids Res.* 3389-3402, respectively. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as "seeds" for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

While all of the above-mentioned algorithms and programs are suitable for a determination of sequence alignment and % sequence identity, for purposes of the disclosure herein, determination of % sequence identity will typically be performed using the BESTFIT or GAP programs in the GCG Wisconsin Software package (Accelrys, Madison Wis.), using default parameters provided.

The term "NH2 Terminal Modifications" may be used to refer to the peptides described herein. The terminus of the peptide compounds of the invention corresponding to the amino terminus, if present, may be in the "free" form (e.g., $H_2N$—), or alternatively may be acylated with a group of the formula $R^2C(O)$— or $R^2S(O)_2$—, wherein $R^2$ is as previously defined. In one embodiment, $R^2$ is selected from the group consisting of ($C_1$-$C_6$) alkyl, ($C_5$-$C_{10}$) aryl, ($C_6$-$C_{16}$) arylalkyl, 5-10 membered heteroaryl or 6-16 membered heteroarylalkyl.

In another embodiment, the amino terminus may be "blocked" with a blocking group designed to impart the compound with specified properties, such as a low antigenicity. Non-limiting examples of such blocking groups include polyalkylene oxide polymers such as polyethylene glycol (PEG). A variety of polymers useful for imparting compounds, and in particular peptides and proteins, with specified properties are known in the art, as are chemistries suitable for attaching such polymers to the compounds. Specific non-limiting examples may be found in U.S. Pat. Nos. 5,643,575; 5,730,990; 5,902,588; 5,919,455; 6,113, 906; 6,153,655; and 6,177,087, the disclosures of which are incorporated herein by reference.

The term "Carboxy Terminus Modifications" may be used in relation to the peptides described herein. The terminus of the peptide compounds corresponding to the C-terminus, if present, may be in the form of an underivatized carboxyl group, either as the free acid or as a salt, such as a sodium, potassium, calcium, magnesium salt or other salt of an inorganic or organic ion, or may be in the form of a derivatized carboxyl, such as an ester, thioester or amide. Such derivatized forms of the compounds may be prepared by reacting a compound having a carboxyl terminus with an appropriate alcohol, thiol or amine. Suitable alcohols, thiols or amines include, by way of example and not limitation, alcohols of the formula $R^2OH$, thiols of the formula $R^2SH$ and amines of the formula $R^2NH_2$, $R^2R^2NH$ or $NH_3$, where each $R^2$ is, independently of the others, as previously defined.

The term "L or D form amino acids" may be used in relation to the peptide described herein. As will be recognized by skilled artisans, the various $X''$ residues comprising the compounds of the invention may be in either the L- or D-configuration about their $C_\alpha$ carbons. In one embodiment, all of the $C_\alpha$ carbons of a particular compound are in the same configuration. In some embodiments of the invention, the compounds comprise specific chiralities about one or more Co, carbon(s) and/or include non-peptide linkages at specified locations so as to impart the compound with specified properties. For example, it is well-known that peptides composed in whole or in part of D-amino acids are more resistant to proteases than their corresponding L-peptide counterparts. Thus, in one embodiment, the compounds are peptides composed in whole or in part of D-amino acids. Alternatively, compounds having good stability against proteases may include peptide analogs including peptide linkages of reversed polarity at specified positions. For example, compounds having stability against tryptic-like proteases include peptide analogs having peptide linkages of reversed polarity before each L-Arg or L-Lys residue; compounds having stability against chymotrypsin-like proteases include peptide analogs having peptide linkages of reversed polarity before each small and medium-sized L-aliphatic residue or L-non-polar residue. In another embodiment, compounds having stability against proteases include peptide analogs composed wholly of peptide bonds of reversed polarity. Other embodiments having stability against proteases will be apparent to those of skill in the art. Additional specific embodiments of the compounds are described herein.

EXAMPLES

The following examples are illustrative in nature and are in no way intended to be limiting.

Example 1. Experimental Procedures

A. Construction of Sequence-Optimized, Truncated Human CBS in PET29A(+) Vector

As previously described in International Publication No. WO2014120770, the disclosure of which is incorporated herein by reference in its entirety, full length (551 aa) human CBS coding sequence was optimized for bacterial expression and cloned into the pUC57 vector following digestion with the EcoRV restriction enzyme, by GenScript USA Inc (NJ, USA). The CBS sequence was then amplified by PCR using primers A1 and A2 to generate a sequence coding for the truncated enzyme (aa 1-413). The PCR product was then digested with the restriction enzymes NcoI and XhoI, and ligated into the pET-28a(+) vector that was digested with the same enzymes. Cloning into the optimal NcoI site of pET-28a(+) results in a G to C mutation as compared to the CBS wild-type sequence. Site-Directed Mutagenesis kit (Stratagene, Calif., USA) utilizing primers B1 and B2, was used to re-generate the wild type sequence (htCBS). The same strategy was used to generate the C15S mutant (T to A mutation; htCBSC15) by using primers C1 and C2. All sequences were verified by sequencing. Expression of the truncated CBS is controlled by an upstream T7 promoter in the pET-28a(+) vector, which requires transformation into DE3 bacteria and induction by IPTG. Table 1 describes the primers and their sequence identifier.

TABLE 1

| Primers | |
| --- | --- |
| Primer name | SEQ ID NO. |
| A1 | 7 |
| A2 | 8 |
| B1 | 9 |
| B2 | 10 |
| C1 | 11 |
| C2 | 12 |
| pKK-F (SphI) | 5 |
| pKK-R (Kpn I) | 6 |

B. Expression and Purification

The pET-28a(+) vector, harboring the sequence coding for the truncated human CBS, was transformed into DE3 bacteria, i.e. *E. Coli* BL-21 (DE3) or HMS174(DE3), and bacteria from kanamycin-resistant clones were grown in 5 ml of Luria-Bertani (LB) medium, with 30 ug/ml kanamycin, overnight at 37° C. on a rotational shaker at 275 RPM. One ml of the overnight culture was added to a 100 ml Terrific Broth (TB) medium with 30 ug/ml kanamycin and grown overnight. 10 ml of was then added to a 1 liter TB medium containing 0.001% of thiamine-HCl pH 8.0, 0.0025% of pyridoxine-HCl pH 8.0, 0.3 mM δ-ALA pH 8.0, 150 µM ferric chloride, 30 ug/ml of kanamycin. The culture was then grown at 30° C. on a rotational shaker at 275 RPM until $OD_{600}$ reached the value of ~0.6-0.7 and protein expression was induced by addition of 1 mM IPTG. Fermentation was continued for additional 16 hours. Cells were harvested by a 10 minutes, 6000 RCF centrifugation at 4° C., washed with ice-cold 0.9% NaCl, re-centrifuged as above, and frozen at −80° C. 4.45 ml of lysis buffer (20 mM $NaH_2PO_4$, pH=7.2, 40 mM NaCl, 0.1 mM PLP) per 1 gram of pellet was then added to the cell pellet and the latter was homogenized in a Dounce homogenizer and treated with lysozyme (2 mg/ml final), incubated for 1 hour at 4° C. on a rocking platform, sonicated to reduce viscosity, and centrifuged at 53000 RCF. The supernatant, comprising the soluble fraction was then stored at −80° C. The lysate was processed through a multi-step chromatographic procedure. The core process consists of an anion exchange capture column (DEAE Sepharose-FF), followed by an affinity column. This attains purity of approximately 90%. The final purity of >99% is achieved by the use of one or two polishing chromatography steps. The final column eluate was diafiltered into PBS.

C. Enzyme Activity Assay

CBS activity was determined by a radioisotope assay with $C^{14}$-labeled serine as a substrate. Ten µl (total 490 ng) of pure htCBS in dilution buffer (0.1 M Tris-HCl pH=8.6, 1 mM DTT, 10 µM PLP, 0.5 mg/ml BSA) or 10 µl of plasma were added to 85 µl of reaction mixture containing 0.1 M Tris-HCl pH=8.6, 10 mM L-serine, 0.5 mM PLP, 0.5 mg/ml BSA and 0.3 µCi (for pure enzyme) or 0.45 µCi (for plasma) of L-[$C^{14}$(U)]-Serine. Samples were incubated for 5 min at 37° C. and reaction was initiated by addition of 5 µl of 0.2 M Hcy (10 mM final concentration). Following 30 min of incubation at 37° C., a 20 µl aliquot of the assay mixture was applied onto a grade 3 CHR Whatman (NJ, USA) paper. The $C^{14}$-cystathionine formed in the reaction was separated from $C^{14}$-serine by an overnight descending paper chromatography in 2-propanol/formic acid/$H_2O$ (75:5.7:18.9 v/v). Radioactivity in the area of the marker cystathionine (detected by staining the marker lane with ninhydrin) was determined by cutting the chromatogram into strips that were submerged in 5 ml of Opti-fluor scintillation cocktail (PerkinElmer, Mass., USA) and counted in a Beckman LS-3801 scintillation counter. For pure enzyme, specific activity values are expressed as enzyme units (the amount of enzyme that produces 1 μmol of cystathionine/hour) per mg of CBS, and for plasma samples as units per μl plasma.

D. In Gel Activity Assay

Protein samples were separated using Native Page (Bio-Rad, Calif., USA). The gel was then incubated for 15-30 minutes in a staining solution (100 mM Tris-HCl pH=8, 20 mM L-cysteine, 50 mM 2-mercaptoethanol, 0.1 mM PLP and 0.2 lead nitrate). Reaction was stopped by submerging the gel in 7% acetic acid.

E. Determination of Metabolite Concentrations

Plasma metabolites homocysteine, cystathionine and cysteine were determined by stable-isotope-dilution liquid chromatography mass spectrometry as previously described in (Allen et al., 1993, *Metabolism*, 42: 1448-1460). Measurements of total non-protein bound homocysteine and other aminothiols as well as of amino acids in tissue were performed as described in (Maclean et al., 2010b. *Mol. Genet. Metab.* 101, 153-162).

F. PEGylation

Polyethylene glycol molecules were purchased from the NOF Corporation (Tokyo, Japan). PEGylation was carried out according to manufacturer instructions. For example, coupling of PEG maleimide derivatives to the SH groups of htCB S (5 mg/ml) was carried out in a 100 mM phosphate buffer pH=6.5 overnight at 4° C. Molar Ratio between PEG molecules to the CBS protein was 10:1 or 5:1.

G. Animal Procedures

All animal procedures were approved by the University of Colorado-Denver IACUC, which is an AAALAC Accredited (#00235), Public Health Service Assured (# A 3269-01) and USDA Licensed (#84-R-0059) Institution. C576BL/6J and CBS knock out (KO) mice were obtained from the Jackson Laboratory (ME, USA). Human Only (HO) mice were previously generated (Maclean et al., 2010b. *Mol. Genet. Metab.* 101, 153-162). Animals were maintained on extruded standard diet 2920X (Harlan, Calif., USA). Representative pups were routinely analyzed for homozygosity. A single-use lancet for submandibular bleeding was used for blood collection into Capiject T-MLHG lithium heparin (12.5 IU) tubes with gel (Terumo Medical Corporation, N.J., USA). Tubes were then centrifuged at 1200G for 10 min, followed by collection of plasma to 1.5 ml tubes and storage at −80° C.

Genotyping: Representative pups were routinely analyzed for homozygosity qPCR. Tail biopsies were generated by the DNeasy Blood and Tissue kit (Qiagen, Hilden, Germany). DNA quality was monitored by NanoDrop 1000 (Thermo Scientific, Del., USA). Twenty ng samples of DNA were run single-plex in triplicate using Applied Biosystem's (CA, USA) Gene Expression master mix (Item #4369016). Amplification was performed on Applied Biosystem's 7500 Fast Instrument using the standard curve method. Applied Biosystems' Tert (Item #4458366) or Tfrc (Item #4458368) copy number reference assays were used as the homozygous one copy calibrator. Applied Biosystem's assay Mr00299300 was used to detect the Neo gene.

Example 2. htCBS Retention Time

A. Unmodified htCBS Exhibits a Short Retention Time in Circulation

The pharmacokinetic properties of a pharmacologically active substance that is administered to circulation is greatly affected by natural mechanisms of ADME. Rapid clearance of the injected molecule may greatly impact treatment efficacy and thus longer circulating half-lives are desired, which may translate into less frequent administrations or smaller doses that in turn minimize the side effects. To determine the pharmacokinetics of htCBS in plasma circulation, a single dose of 5 mg/kg was injected via subcutaneous (SQ), intravenous (IV) or intraperitoneal (IP) routes to C57BL/6J mice. Administration of htCBS via IV or IP routes exhibited the highest specific activity values during the first 4 hours post injection (observed peak plasma levels of up to 123 and 76 mU/μL, respectively; Table 2 shows Area Under Curve (AUC) values). The pharmacokinetic parameters calculated from plasma samples (Table 2) show that the half-life for htCBS was 2.7 hours, suggesting that after roughly 6 half-lives (less than 20 hours) htCBS levels should be undetectable.

The bioavailability of htCBS was 50% for SQ routes suggesting that SQ delivery may be a clinical option for this therapeutic approach. The slower apparent half-lives for SQ and IP (Table 2) can be explained by a slow absorption phase that is occurring during the elimination phase thereby extending the mean residency time and apparent half-life, however, for the present purpose a much longer half-life was desirable and thus PEGylated derivatives of htCBS were tested.

TABLE 2

| Pharmacokinetic Parameters | | | | |
| --- | --- | --- | --- | --- |
| Pharmacokinetic Parameter | Units | IP | SQ | IV |
| Dose Amount | Mg/Kg | 5 | 5 | 5 |
| AUC(0-t) (obs area) | mU-hr/μL | 932.4 | 500.9 | 1011 |
| Bioavailability | % | 92% | 50% | — |
| E Half-life | hr | 4.3 | 6.1 | 2.7 |
| Cmax (obs) | Mu/μL | 75.9 | 34.5 | — |
| MRT (area) | hr | 7.9 | 9.5 | 4.9 |

Figure 1B:
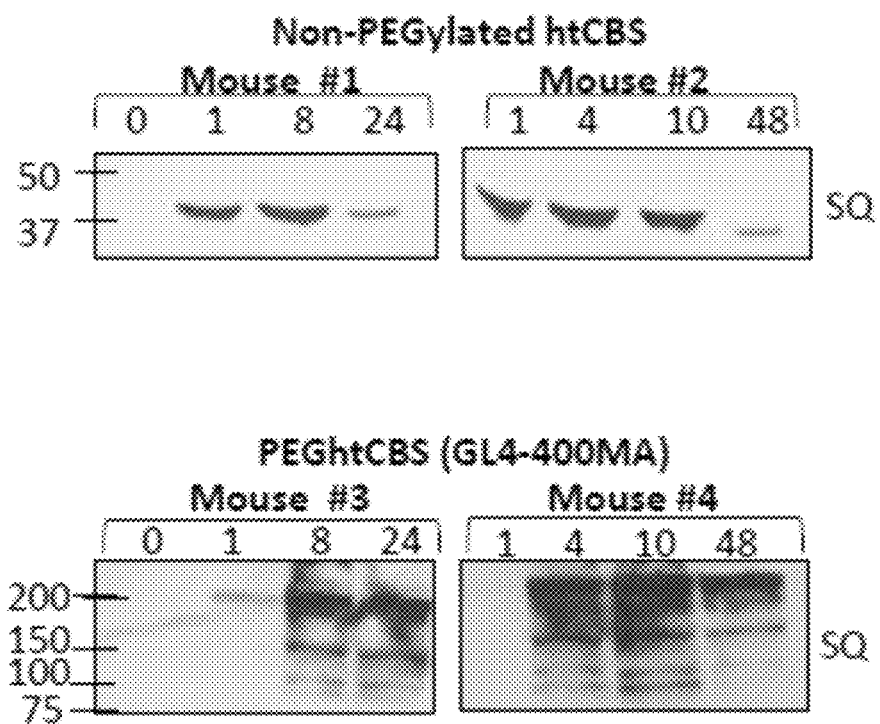

The rapid decline in htCBS activity in vivo may be attributed to a facilitated clearance from circulation and may also be attributed to the loss of enzymatic activity of htCBS once introduced to the environment in circulation. To test the latter, htCBS was incubated in vitro in mouse plasma of wild type or HO mice at 37° C. for up to 96 hours, with activity measured every 24 hours. As shown in FIG. 1A, no significant loss of activity was recorded for up to 72 hours of incubation in the plasma of either mouse model. A modest 25% loss of activity was recorded after 96 hours of incubation. Furthermore, as shown in FIG. 1B, western blot (WB) analyses of plasma from the SQ injected animals, revealed that the amount of htCBS decreases as a function of time, hence, clearance accounts for the rapid loss of htCBS activity in circulation, rather than loss of activity in plasma.

B. PEGylation of htCBS Enhances Plasma Half-Life In Vivo

In order to determine the impact of PEG molecules on the pharmacokinetics CBS, htCBS was PEGylated with a low molecular weight (2 kDa) linear PEG, and with a high molecular weight (40 kDa) four arm branched PEG (designated ME020MA and GL4-400MA, respectively). As shown in Table 3, PEGylation did not affect the specific activity of the enzyme. Table 3 shows the results of the Coomassie-stained SDS-PAGE of the PEGylated and non-PEGylated htCBS with corresponding specific activity values showing that PEGylation does not influence the activity of the enzyme. Mice were injected SQ as described in A (n=4-5), with the ME200MA- or GL4-400MA-PEGylated htCBS as compared to the non-PEGylated htCBS.

TABLE 3

| htCBS tested | Activity |
| --- | --- |
| | Specific Activity |
| Non-PEG CBS | 1193 |
| ME-200MA CBS | 1184 |
| GL4-400MA CBS | 1075 |

A dose of 5 mg/kg body weight (BW) of PEGylated htCBS (PEGhtCBS) was administered to C57BL/6J mice via the SQ and IV route, and CBS activity was monitored at different time points. Two experimental arms (n=5 each) were used for each injection route. Blood was collected post injection from group 1 at 0, 1, 8 and 24 hours and from group 2 at 1, 4, 10, and 48 hours.

As shown in FIG. 1B (bottom panel) for the GL4-400MA PEGhtCBS, the activity in plasma was significantly extended for the PEGylated protein as compared to the non-PEGylated counterpart. As shown in Table 4 the half-life increased from 2.7 hours for the non-PEGylated htCBS to 16.7 and 30.4 hours with the ME020MA and GL4-400MA PEGylation, respectively.

TABLE 4

Pharmacokinetic Modeling Results

| | | Pharmacokinetic Modeling Results | | | |
| --- | --- | --- | --- | --- | --- |
| | | PEGylated htCBS ME020MA | | PEGylated htCBS GL400MA | |
| Parameter | Units | SQ | IV | SQ | IV |
| Dose Amount | Mg/Kg | 5 | 5 | 5 | 5 |
| AUC(0-t) (obs area) | Mu-hr/μL | 1637.0 | 3193.2 | 2286.3 | 2836.5 |
| Bioavailability | % | 51.2% | — | 80.6% | — |
| E Half-life | hr | 15.1 | 16.7 | 20.1 | 30.4 |
| Cmax (obs) | Mu/μL | 54.6 | — | 64.9 | — |
| MRT (area) | hr | 27.0 | 25.7 | 37.0 | 43.1 |

This means that the time of exposure after a single dose would be 5 to 10-fold longer for the PEGylated forms. Additionally, the bioavailability after SQ administration ranged from 50 to 80% suggesting that the SQ route would be reasonable for clinical studies.

Example 3. Administration of htCBS and Serum Levels of Homocysteine, Cystathionine and Cysteine The ultimate goal for the use of htCBS for CBSDH is to lower the toxic tHcy load, to elevate cystathionine and cysteine levels. These changes are expected to prevent, reverse or delay the onset of CBSDH symptoms. Homocystinuria research, however, has long been hindered by a lack of a suitable animal model. Mice that are complete knockout for the mouse gene die within 2-3 weeks after birth. The HO (Human Only) mice are different from other knockout mice because, in addition to having the mouse gene knocked out, they express low levels of the human gene which allows their survival to adulthood (Maclean et al., 2010b. *Mol. Genet. Metab.* 101, 153-162). HO mice exhibit severe elevations of Hcy, methionine, S-adenosyl-methionine, and S-adenosylhomocysteine and present with a concomitant decrease in plasma and hepatic levels of cysteine. Accordingly these mice exhibit characteristics that in several aspects, recapitulate the disease as it occurs in humans.

A. htCBS Administration does not Improve tHcy and Cystathionine Concentrations

Figure 2:
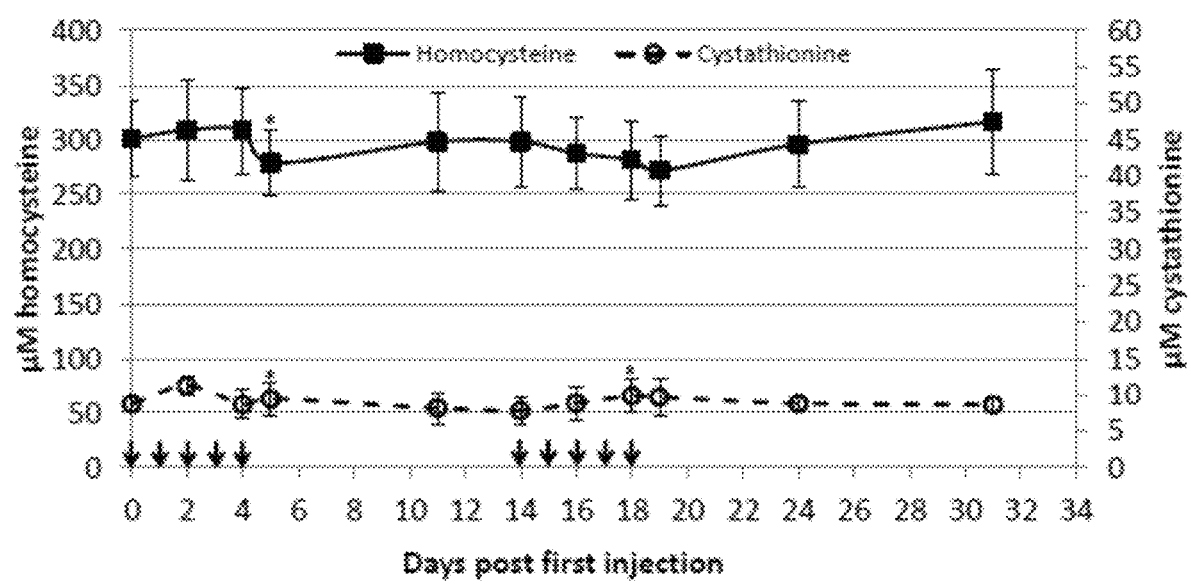
FIG. 2 shows that repeated administration of non-PEGylated htCBS results in no changes in homocysteine or cystathionine levels in HO mice.

HO mice administered non-PEGylated htCBS at 5 mg/kg for 5 consecutive days on weeks 1 and 3 (10 days between sets of treatments) demonstrated no change in serum homocysteine levels. FIG. 2 shows the mean homocysteine and cystathionine levels in HO mice. This lack of metabolic modulation by non-PEGylated htCBS further confirms the necessity to modify htCBS by covalent attachment of polyethylene glycol molecules.

Figure 3:
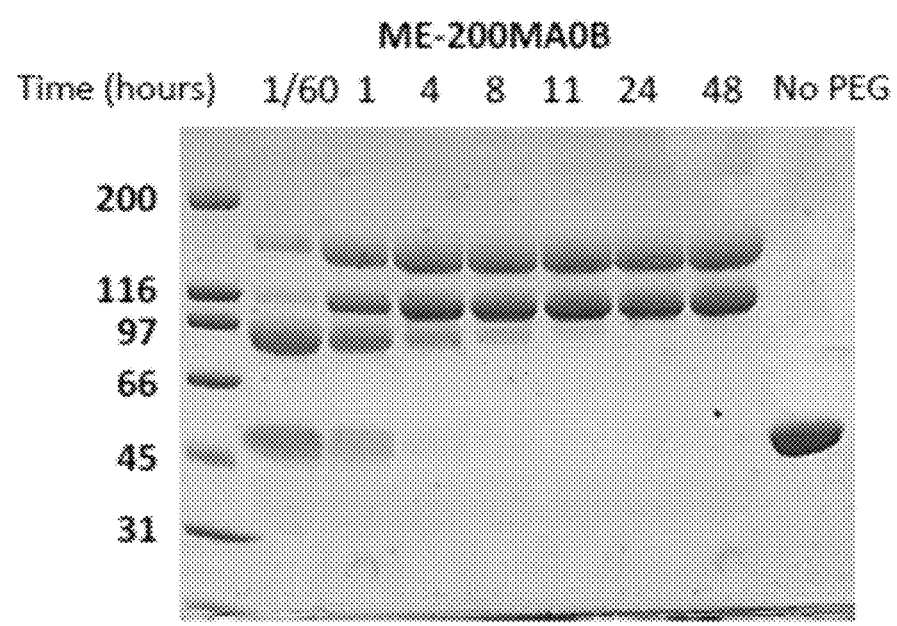
FIG. 3 shows a PEGylation time course with the selected linear 20 kDa PEG molecule designated ME200MAB.

Several different chemistries of PEGs were tested as described in International Publication No. WO2014120770, the contents of which are herein incorporated by reference in its entirety, (See Table 5) and the data indicate that CBS that is PEGylated with lower than 20 kDa PEGs demonstrates a more rapid loss of activity in plasma, than CBS with PEGs of higher molecular weight. For that reason, the linear 20 kDa PEG designated ME200MA0B was chosen for further analyses. FIG. 3 presents a Coomassie-stained SDS-PAGE showing the time course of htCBS PEGylation with ME200MA0B. PEGylation reaction was initiated by adding the PEG, and samples were withdrawn from the tube at the indicated time points to be analyzed.

TABLE 5

PEG chemistry evaluation

| PEG molecule | Structure | Target group | Size (kDa) |
| --- | --- | --- | --- |
| ME020MA | linear | —SH | 2 |
| ME050GS | linear | —NH2, —OH, —SH | 5 |
| ME200GS | linear | —NH2, —OH, —SH | 20 |
| ME200MA0B | linear | —SH | 20 |
| ME400MA | linear | —SH | 40 |
| GL2400MA | 2 arms | —SH | 40 |
| GL4400MA | 4 arms | —SH | 40 |
| GL2800MA | 4 arms | —SH | 80 |

B. Repeated PEGhtCBS Administration Improves tHcy and Cystathionine Concentrations and Restores Normal Cysteine Levels.

Figure 4A:
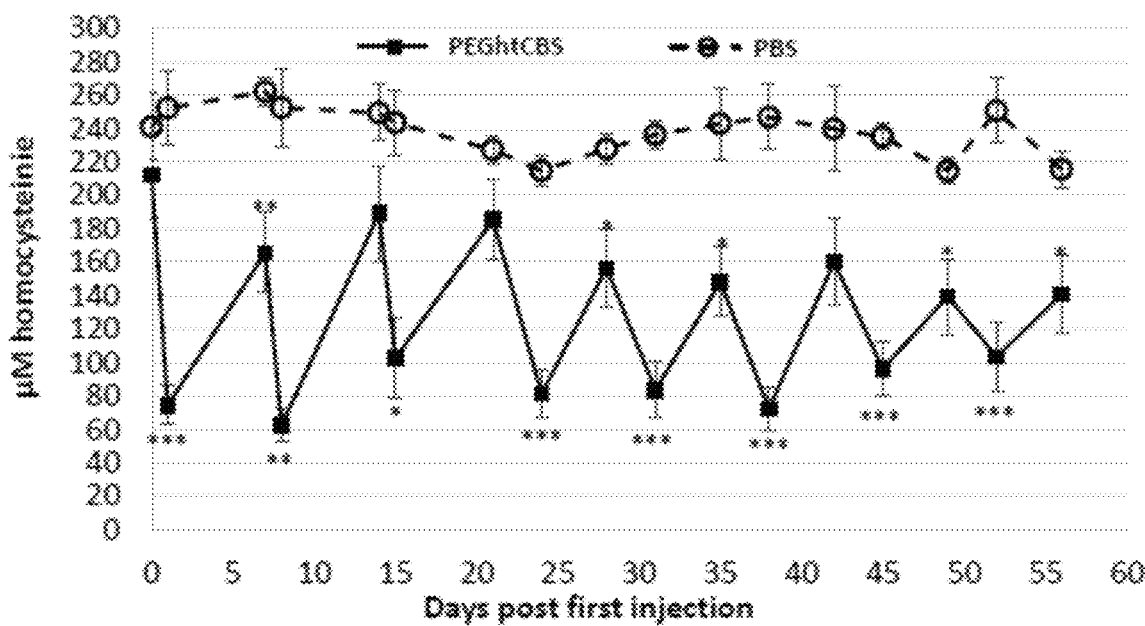
FIG. 4A-4D show that long term repeated injection of the PEGylated htCBS significantly impacts homocysteine, cystathionine and cysteine plasma and tissue levels.
Figure 4B:
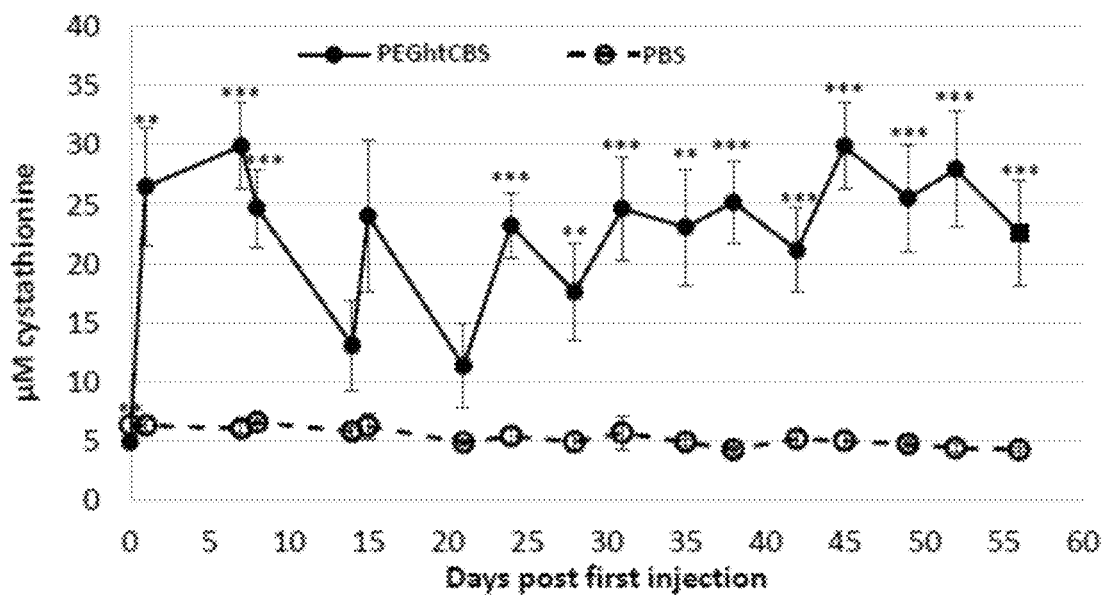
Figure 4C:
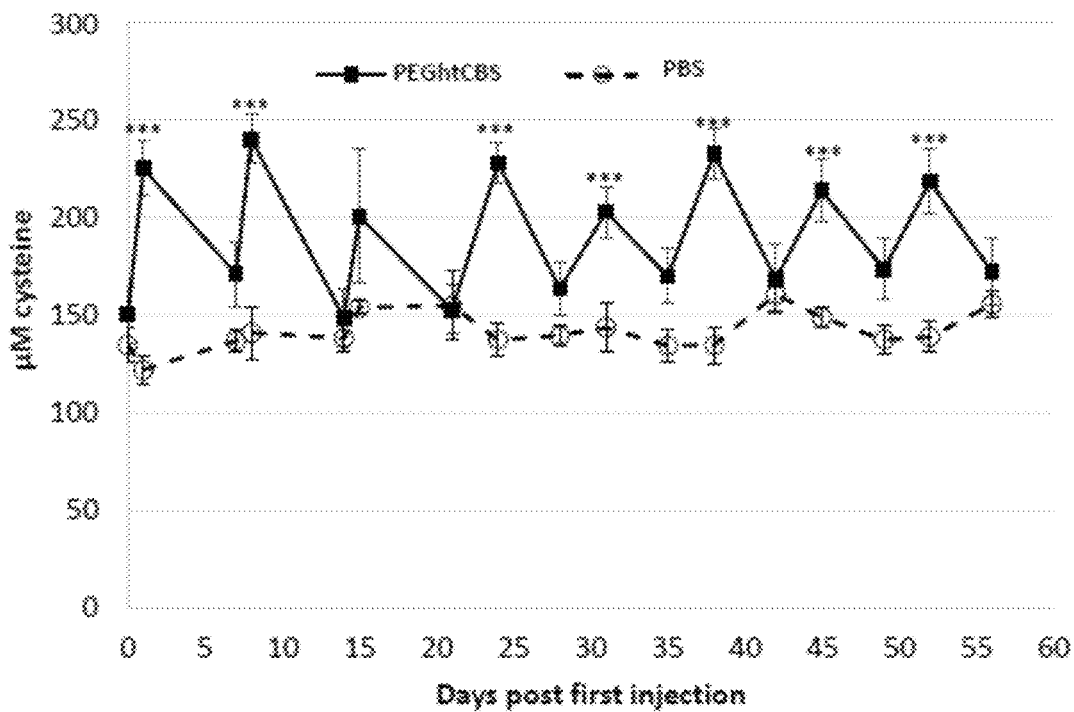
Figure 4D:
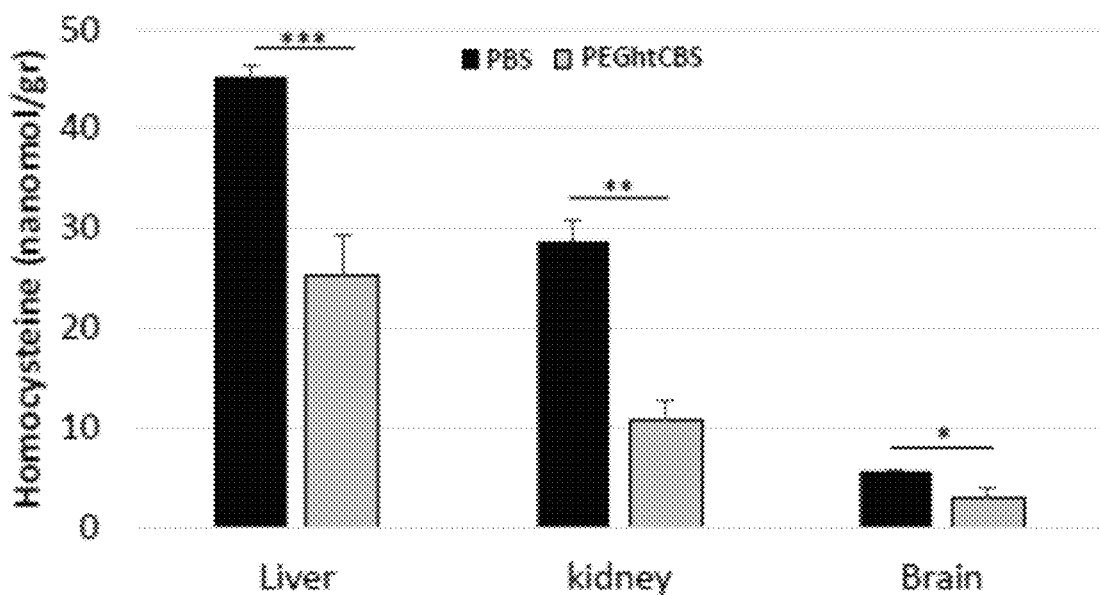

The long term effect of PEGhtCBS administration was monitored using HO mice. The PEGhtCBS enzyme was administered to 8 HO mice at a dose of 7.5 mg/kg, twice a week (Monday and Thursday) for the first two weeks, and then three times a week (Monday, Wednesday and Friday) for 6 weeks. Blood samples were collected 24 hours (Tuesday) and 72 hours (Monday) post injection (FIG. 4A-4C). FIG. 4A shows that plasma tHcy was reduced from 212 μM at time 0 to an average in the range of 62-103 μM 24 hours after injections, and was at a range of 141-189 μM 72 hours post the last weekly injection. From day 28 on, the 72 hour post injections values were significantly lower than the time 0 value (P≤0.02). Cystathionine and cysteine levels were positively influenced as well. Cystathionine increased from 6 μM to as high as 30 μM and cysteine was constantly above 200 μM 24 hours post injection (FIG. 4C). Interestingly, from day 24 on, fluctuations in cystathionine concentration were much less pronounced as compared to the first three weeks of treatment. In addition to analysis of plasma metabolites levels, liver, kidney and brain tissue samples from the injected mice were analyzed as well to determine the levels of non-protein bound homocysteine (free and disulfide-linked forms). As shown in FIG. 4D, in the long term injected animals, a reduction of 44%, 63% and 47% was demonstrated for liver, kidney, and brain tissues, respectively. Thus, long term repeated injection of the PEGhtCBS significantly impacts homocysteine, cystathionine and cysteine plasma levels.

Figure 5A:
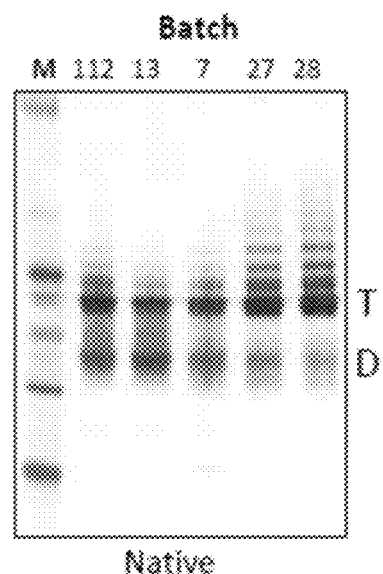
FIG. 5A-5H illustrate that the PEGylated htCBS mutant (also referred to as PEGC15S) and PEGylated htCBS prevents protein aggregation, forms mainly dimers and exhibits a reproducible PEGylation pattern.
Figure 5B:
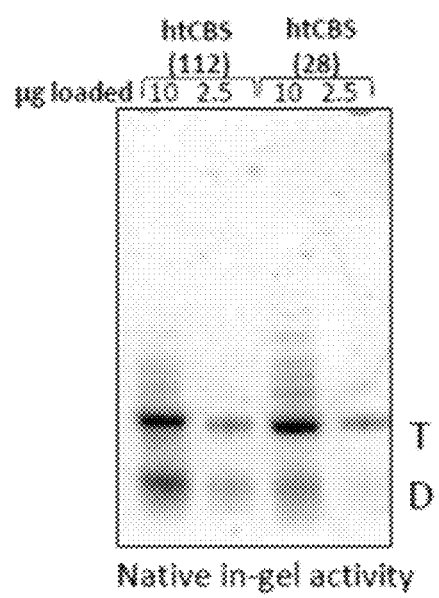
Figure 5C:
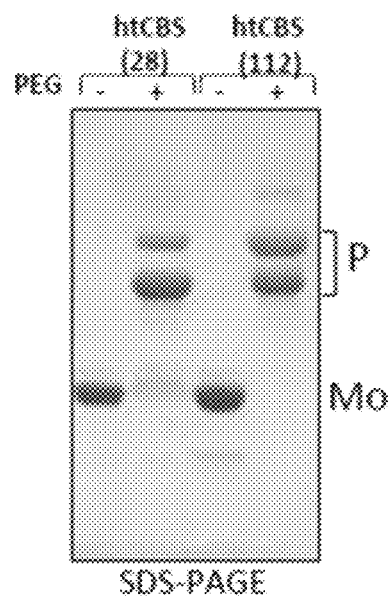
Figure 5D:
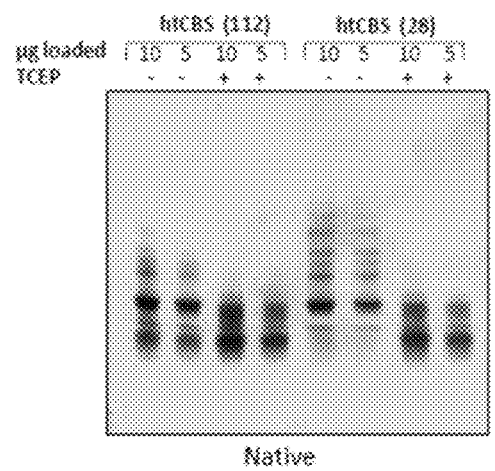
Figure 5E:
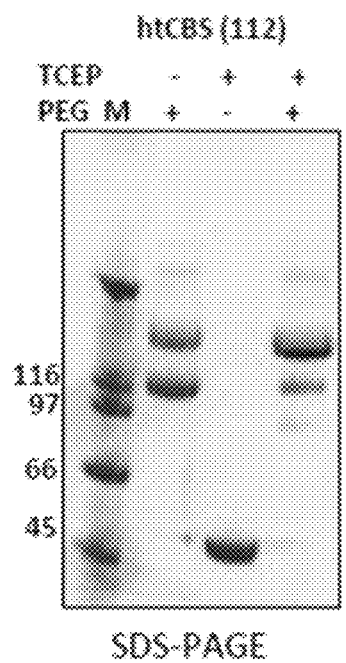
Figure 5F:
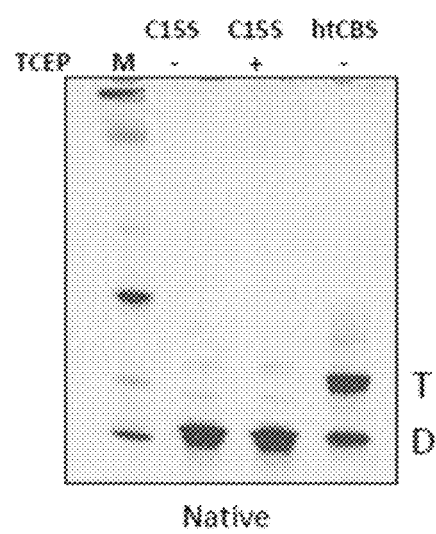
Figure 5G:
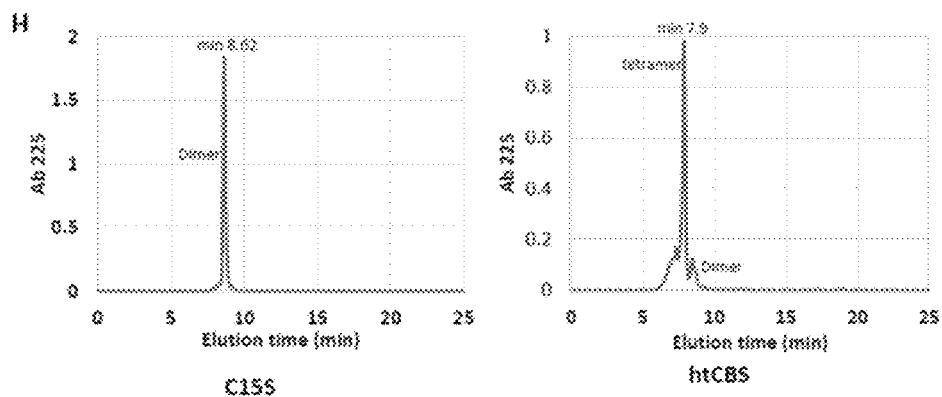
Figure 5H:
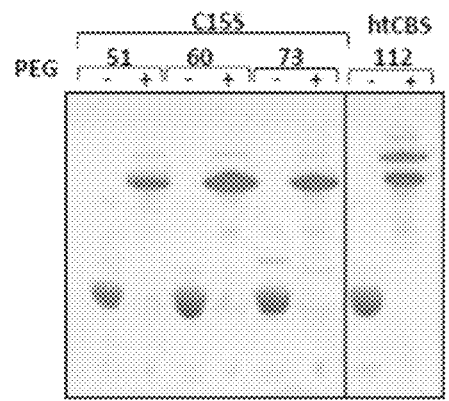

Example 4. htCBS Mutant (C15S) Shows Preferential Aggregation and PEGylation Patterns A. C15S Mutated htCBS Exhibits No Aggregation and a Uniform PEGylation Pattern Although it was previously reported that the htCBS enzyme is less prone to aggregation as compared to the full length protein (Frank et al., 2006, *Biochemistry* 45:11021-11029), it still forms tetramers and higher aggregates. This may stimulate immune defensive mechanisms and lead to e.g. amyloid deposition (D'Souza et al., 2014, "Amyloid: the international journal of experimental and clinical investigation. The official journal of the International Society of Amyloidosis" 21:71-75), but also affect purification, handling, and consistency. FIG. 5A (previously disclosed as FIG. 5A of WO2014120770, the contents of which are herein incorporated by reference in its entirety) depicts a Coomassie-stained native-PAGE showing that different batches of htCBS exhibited different dimer/tetramer ratios, with varying degrees of higher aggregates. FIG. 5B (previously disclosed as FIG. 5B of WO2014120770, the contents of which are herein incorporated by reference in its entirety) is an in-gel activity assay demonstrated that these aggregates exhibit CBS activity. FIG. 5C (previously disclosed as FIG. 5C of WO2014120770, the contents of which are herein are incorporated by reference in its entirety) shows that aggregation causes non-consistent PEGylation products. PEGylation resulted in two distinct bands, presumably reflecting varying degrees of PEGylation as aggregation may act to obscure the available PEGylation sites. Accordingly, due to a more pronounced aggregation of batch 28 (FIG. 5A) its PEGylation resulted in a more pronounced lower band, i.e. less PEGylated, on SDS-PAGE (FIG. 5C), whereas PEGylation of batch 112, comprised of both tetramers and dimers (FIG. 5A), resulted in a more pronounced upper band as compared to batch 28 (FIG. 5C). FIG. 5D shows a Coomassie-stained native gel, indicating that incubation of both enzyme batches with the reducing agent tris(2-carboxyethyl) phosphine (TCEP) converted much of the tetramers and higher aggregates to a dimeric form. These data imply that aggregation is driven by exposed cysteines on the surface of htCBS. Thus, TCEP treatment was believed to also result in a more extensive PEGylation, as more dimers are generated from higher MW forms, giving rise to exposure of additional PEGylation sites on the surface of htCBS. Indeed, as shown in FIG. 5E the ratio between the upper/lower PEGylation bands on a Coomassie-stained SDS-PAGE is significantly shifted towards the upper band following TCEP treatment as compared to PEGylation in the absence of TCEP. Accordingly, htCBS aggregation is believed to be driven, at least partially, by formation of intramolecular disulfide bridges. Thus, C15 was mutated to serine, generating the C15S htCBS mutant; C15 was previously shown to be the most reactive cysteine on the surface of CBS (Frank et al., 2006, Biochemistry 45:11021-11029). FIG. 5F (previously disclosed as FIG. 6A of WO2014120770, the contents of which are herein incorporated by reference by its entirety) depicts a Coomassie-stained native gel, in which two main bands (dimers and tetramers) are observed for htCBS whereas the C15S htCBS mutant exhibits a single band, which as expected is not affected by treatment with TCEP. This observation was further substantiated by HPLC size exclusion chromatography (HPLC-SEC). CBS preparations were separated on a Yarra SEC-3000, 300*7.8 mm size exclusion column (Phenomenex, Calif., USA). The column was calibrated and operated in 100 mM sodium phosphate pH=6.8, at a flow rate of 1 ml/min at room temperature. HPLC-SEC analysis, FIG. 5G (previously disclosed as part of FIG. 7A and FIG. 7B of WO2014120770, the contents of which are herein incorporated by reference in its entirety), shows the differences in htCBS C15S (FIG. 5G, left panel) and htCBS dimer/tetramer ratio (FIG. 5G, right panel). The single peak for the dimeric C15S htCBS mutant eluted at 8.62 min while the main peak for the htCBS eluted at 7.9 min, corresponding to a tetramer. FIG. 4H shows a Coomassie-stained SDS-PAGE gel showing reproducibility of htCBS C15S PEGylation between different batches and comparison to htCBS. The absence of aggregates in the C15S htCBS resulted in a more consistent PEGylation pattern between different batches with almost exclusively one PEGylated band that appears on SDS-PAGE. Direct comparison between PEGhtCBS and the PEGC15S both in vivo and in vitro showed no difference in performance.

Figure 6A:
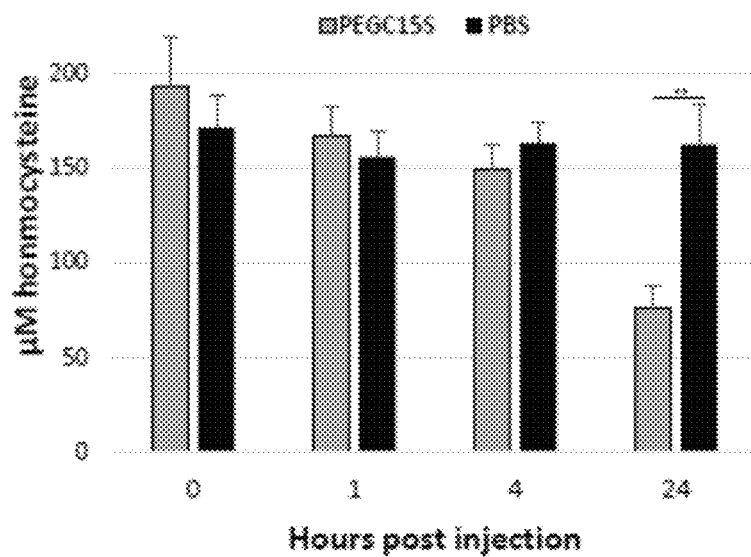
FIG. 6A-6C show the effect of PEGylated htCBS mutant (also referred to as PEGC15S) on homocysteine and its metabolites at 1, 4 and 24 hours post injection.
Figure 6B:
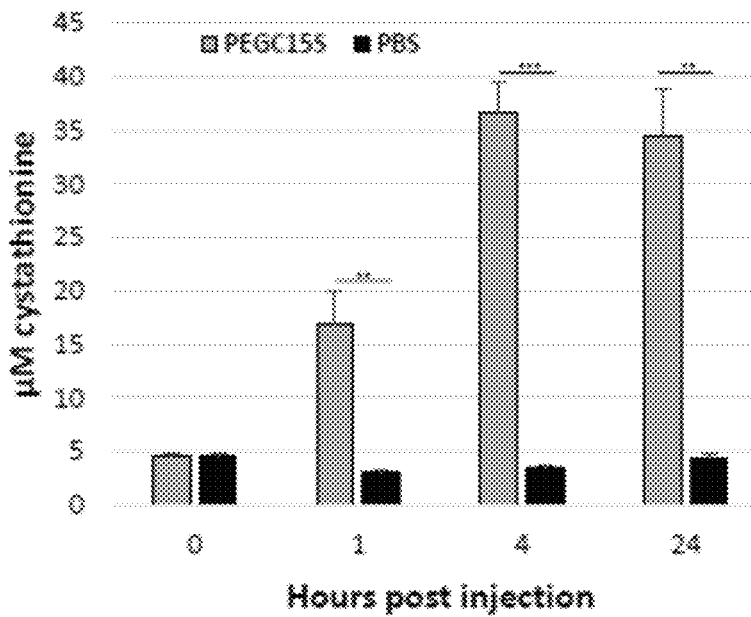
Figure 6C:
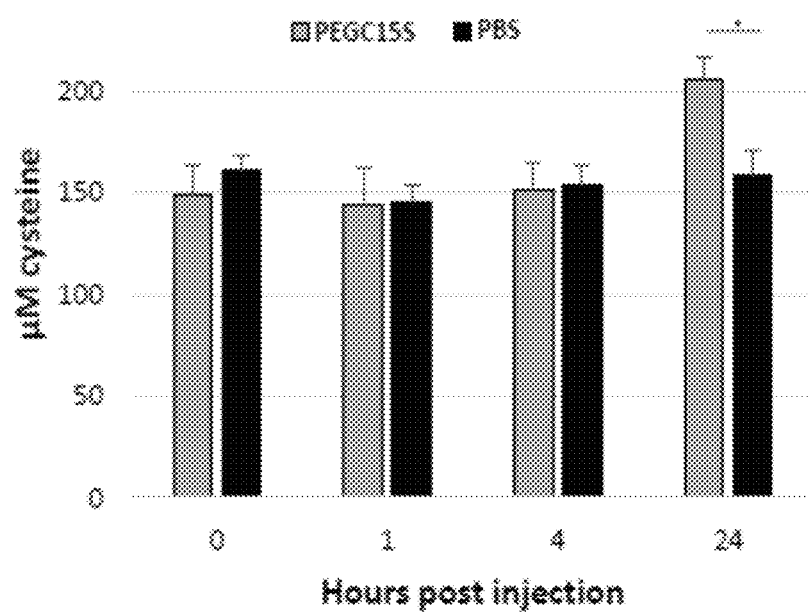

The effect of PEGC15S on metabolites was also tested at 1, 4 and 24 hours post injection (FIG. 6A-FIG. 6C). The levels of tHcy (FIG. 6A), cystathionine (FIG. 6B), and cysteine (FIG. 6C) in HO mice injected with 7.5 mg/kg of PEGC15S or PBS (n=5) 1, 4 and 24 hours post injection were measured. Data is presented as mean±SEM and each time point is compared between the two groups using unpaired Student's t test. *p=0.05, p≤0.01, and *p≤0.001. The effect on tHcy and cysteine was observed only 24 hours post injection (FIG. 6A and FIG. 6C), however a significant increase in cystathionine was already observed at 1 and 4 hours post injection (FIG. 6B).

Example 5. PEGC15S and Betaine Operate Synergistically In Vivo

To evaluate the effect of betaine and the combination therapy, betaine, PEGC15S, and a combination of betaine+PEGC15S treatments were conducted and metabolites of the transsulfuration pathway were compared.

Figure 7A:
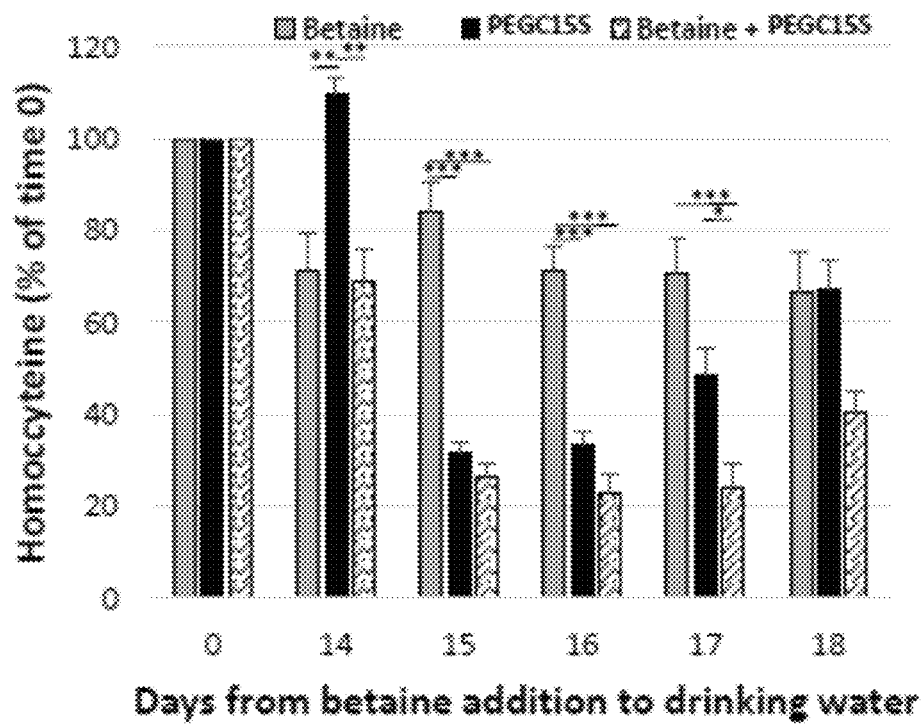
FIG. 7A-7B show that treatment with PEGylated htCBS mutant (also referred to as PEGC15S) and betaine synergistically reduce and maintain low homocysteine levels in HO mice and their effect on cystathionine levels.
Figure 7B:
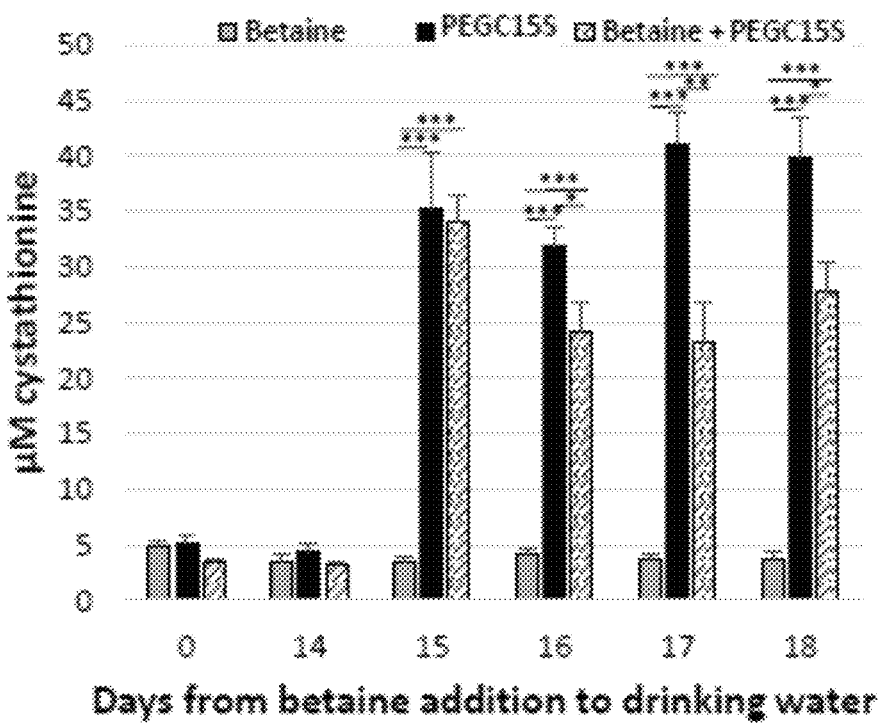

The betaine and betaine+PEGC15S groups were treated with 2% betaine in the drinking water throughout the 18 days of the experiment, and the latter group was injected with 7.5 mg/kg PEGC15S on days 14 and 15. The PEGC15S single treatment group was maintained on regular water and injected on days 14 and 15 as well. As shown in FIG. 7A, 14 days of betaine treatment resulted in a 29% and 32% decrease in tHcy for the betaine treated groups. The betaine single treatment group maintained these levels of tHcy to day 18. Injection of the PEGC15S on the background of betaine resulted in a more pronounced reduction of 74%, 77%, 76% and 40% on days 15, 16, 17 and 18, respectively. Treatment with PEGC15S alone resulted in a reduction of 69%, 67%, 52% and 33% on days 15, 16, 17 and 18, respectively. According to these data, injection of PEGC15S with or without betaine treatment is far superior to betaine treatment alone. In addition, the combination of betaine+PEGC15S was superior to treatment with PEGC15S alone. As shown in FIG. 7B, the difference between these two groups became statistically significant 48 hours post second injection (on day 17). Thus, the combination of PEGC15S with betaine allows for maintaining lower tHcy levels for an extended period of time.

Betaine treatment alone did not result in an increase of cystathionine throughout the 18 days of the experiment. In contrast, an increase was observed for the two groups that were treated with the PEGC15S (with or without betaine). Interestingly, the combination of PEGC15S with betaine, resulted in an increase which starting on day 16 and on, was significantly lower than in the group that received PEGC15S single therapy. This is due to the fact that treatment with PEGC15S alone channels homocysteine to condensation with serine to form cystathionine. Combination with betaine channels some of the available homocysteine through the re-methylation pathway to produce methionine, and thus less homocysteine may be available for PEGC15S to be converted to cystathionine.

Example 6. PEGC15S Rescues KO Mice from Early Death and Improves Liver Disease

A. Reduction of Early Death

Figure 8A:
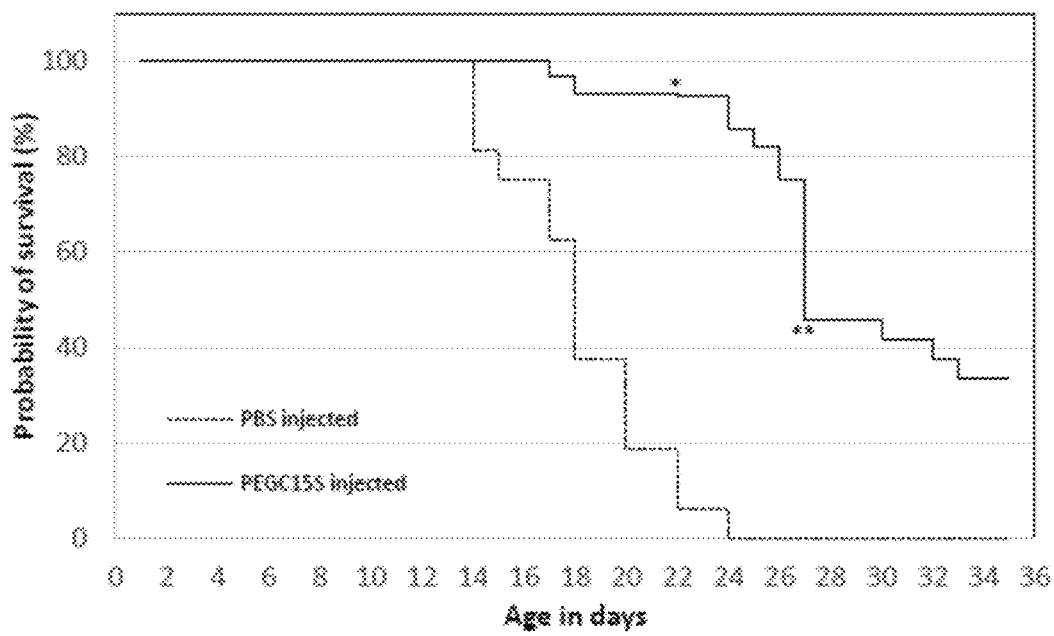
FIG. 8A-8B show that PEGylated htCBS mutant (also referred to as PEGC15S) administration rescues CBS complete knockout mice from early lethality and ameliorates liver pathology.

The majority of complete CBS-knockout mice (KOs) die within 2-3 weeks after birth. A Kaplan Meyer survival curve of KO mice injected twice weekly with PEGC15S versus mice that were injected with PBS was plotted. Mice were maintained on betaine water until day 21, and the ability of the injected enzyme to rescue KO pups was tested. KO pups were injected twice weekly with PEGC15S or with PBS. All mice were on betaine in drinking water up to day 21 (weaning day). As shown in FIG. 8A, on day 21, only 18% of the mice survived in the PBS-injected group as opposed to 93% of those that were injected with the enzyme. No PBS-injected animal survived to day 24, while 86% survival was recorded for the enzyme-injected group. From day 24 and on, the numbers of the enzyme-injected animals began to decline as well, with 45% survival on day 29 and 33% on day 35.

B. Liver Disease

It was previously demonstrated that KO mice suffer severe liver damage (Maclean et al., 2010a, *Mol. Genet. Metab* 101, 163-171; Watanabe et al., 1995, *Proc. Natl. Acad. Sci. U.S.A.* 92:1585-1589). Prolonged survival of KO mice, may be thus correlated with improvement in liver disease after CBS treatment. Accordingly, histological analysis of liver sections from animals that were injected with PEGC15S for 35 days were performed. Animals were sacrificed on day 36 and liver samples were processed for histological analysis by optical microscopy. PBS-injected animals did not survive to day 35, but liver samples were taken from two animals immediately after death, and were processed. The experiments were carried out in a blinded fashion. Livers were removed and were fixed for 24 hours with 4% paraformaldehyde in PBS (pH 7.4). Tissue blocks for histology were trimmed, dehydrated with an ethanol series followed by acetone, acetone-xylene mixture and xylene and then embedded in paraffin. In parallel, small tissue blocks (around 4 mm×2 mm) fixed with paraformaldehyde were rapidly frozen in petrol ether cooled with dry ice, and stored at −50° C. for detection of apolar lipids.

Paraffin sections 4 μm thick were deparaffinized in xylene and after isopropyl alcohol step rehydrated with ethanol (96%, 70%, 60%). Tissue sections were stained with hematoxylin and eosin (H&E) to evaluate histopathological changes. Masson trichrome staining was performed for detection of fibrosis. Steatosis was verified using Oil Red O staining for detection of apolar lipids in fixed-frozen sections, 10 μm thick and cut with a Leica Cryomicrotome (CM 1850). The sections were viewed and photographed in a Nikon light microscope (E800) equipped with Olympus digital camera (DP70).

Figure 8B:
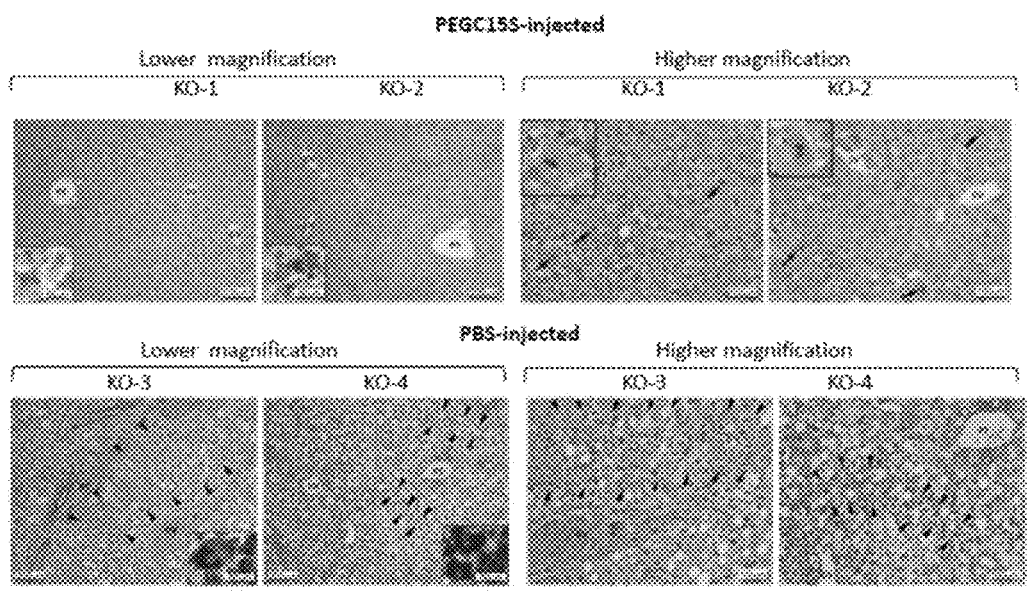

FIG. 8B shows the liver histology of two PEGC15S-injected KO mice sacrificed on day 35 versus livers from two PBS-injected KO animals that died on days 17 and 24 (hematoxylin and eosin stain). Low power views of the liver parenchyma (FIG. 8B, left columns) show moderate changes with slightly irregular liver cell plates and mild to moderate steatosis in PEGC15S-injected KO-1 and KO-2 contrasting with massive zonal necroses of hepatocytes (FIG. 8B, KO-3, marked by arrowheads) and diffuse steatosis with multiple dispersed necroses (FIG. 8B, KO-4, necroses marked by arrowheads) in PBS-injected KOs. A specific stain for apolar lipids in the cytoplasm of hepatocytes is shown in the inserts. Higher power views (right columns) demonstrate presence of frequent mitoses (marked by arrows and showed in a detail in inserts) and enlarged pleiomorphic nuclei with prominent nucleoli in PEGC15S-injected KOs. Higher power views of the liver parenchyma in PBS-injected KOs demonstrate confluent hepatocellular necroses with a sparse inflammatory infiltration (FIG. 8B, KO-3, marked by arrowheads) or multiple dispersed necroses accompanied with a prominent resorptive inflammatory reaction (FIG. 8B, KO-4, marked by arrowheads). The remaining liver parenchyma displays micro and macrovesicular steatosis in PBS-injected KOs. (PT=portal tract, CV=central vein).

PBS-injected animals developed severe hepatopathy characterized by pronounced microvesicular to macrovesicular steatosis and significant death of hepatocytes, with minimal or no fibrosis. Multiple mono or oligo cellular necroses of hepatocytes dispersed throughout the liver lobule accompanied by a prominent inflammatory resorptive reaction were found in one animal, whereas massive confluent necroses of hepatocytes mainly in periportal zones with a sparse inflammatory infiltrate dominated a feature in the other. Signs of liver parenchyma regeneration were minimal in both animals. The two PEGC15S-injected animals showed moderate changes in the liver with minor signs of parenchyma damage but with prominent regeneration, and were correctly recognized by the examiner as receiving therapy. Changes indicative of liver parenchyma regeneration (slightly irregular architecture of the liver lobule, basophilic cytoplasm of hepatocytes, frequent mitoses and binucleated hepatocytes, nuclear pleomorphy and enlargement with prominent nucleoli) were the most conspicuous feature. The overall morphology was consistent with increased proliferation, transcription and translation in hepatocytes. Besides, rare focal necroses of hepatocytes and mild steatosis of a microvesicular type were detected and fibrosis was minimal.

The foregoing examples of the related art and limitations related therewith are intended to be illustrative and not exclusive. Other limitations of the related art will become apparent to those of skill in the art upon a reading of the specification and a study of the drawings.

Compounds useful in the invention include those described herein in any of their pharmaceutically acceptable forms, including isomers such as diastereomers and enantiomers, salts, solvates, and polymorphs, as well as racemic mixtures and pure isomers of the compounds described herein, where applicable.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

All patents, patent applications, patent publications, scientific articles and the like, cited or identified in this application are hereby incorporated by reference in their entirety in order to describe more fully the state of the art to which the present application pertains.

We claim:

1. A method of treating a subject having a condition associated with cystathionine β-synthase deficiency due to a pyridoxine-responsive mutation, the method comprising: administering to the subject an isolated human truncated cystathionine β-synthase (htCBS) mutant polypeptide having a C15S mutation compared to SEQ ID NO: 2, wherein the isolated htCBS mutant polypeptide is PEGylated and the C-terminal regulatory region is truncated.

2. The method of claim 1, wherein the isolated htCBS mutant polypeptide is co-administered with betaine.

3. The method of claim 1, wherein betaine is administered prior to the isolated htCBS mutant polypeptide.

4. The method of claim 1, wherein the htCBS mutant polypeptide forms a dimer.

5. The method of claim 1, wherein the htCBS mutant polypeptide does not form a tetramer.

6. The method of claim 1, wherein treating comprises mitigating or reducing pathological events of the condition associated with cystathionine β-synthase deficiency due to a pyridoxine-responsive mutation in the subject.

7. The method of claim 1, wherein the isolated htCBS is PEGylated with a low molecular weight linear PEG.

8. The method of claim 1, wherein the isolated htCBS is PEGylated with a high molecular weight four arm branched PEG.

9. The method of claim 1, wherein the isolated htCBS is PEGylated with a 20 kDa NHS ester-activated PEG.

10. The method of claim 1, wherein the subject is a partial responder to vitamin B6.

11. The method of claim 1, further comprising administering vitamin B6.

12. A method of treating a disease, disorder, or condition selected from: mental retardation, a psychiatric disturbance, a central nervous system problem, a cardiovascular disease, and a connective tissue disorder, the method comprising: administering to the subject an isolated human truncated cystathionine β-synthase (htCBS) mutant polypeptide having a C15S mutation compared to SEQ ID NO: 2, wherein the isolated htCBS mutant polypeptide is PEGylated and the C-terminal regulatory region is truncated.

13. The method of claim 12, further comprising co-administering betaine with the htCBS mutant polypeptide.

14. The method of claim 12, wherein betaine is administered prior to the isolated htCBS mutant polypeptide.

15. The method of claim 12, wherein the htCBS mutant polypeptide forms a dimer.

16. The method of claim 12, wherein the htCBS mutant polypeptide does not form a tetramer.

17. The method of claim 12, wherein the isolated htCBS is PEGylated with a low molecular weight linear PEG.

18. The method of claim 12, wherein the isolated htCBS is PEGylated with a high molecular weight four arm branched PEG.

19. The method of claim 12, wherein the isolated htCBS is PEGylated with a 20 kDa NHS ester-activated PEG.

20. The method of claim 12, further comprising administering vitamin B6.

21. The method of claim 12, wherein the central nervous system problem is seizures.

22. The method of claim 12, wherein the connective tissue disorder is selected from the group consisting of: progressive myopia, lens dislocation, ectopia lentis, marfanoid habitus, osteoporosis, scoliosis, fine fair hair, and brittle and thin skin.

23. The method of claim 12, wherein the cardiovascular disease is a predisposition to thromboembolic complications.

\* \* \* \* \*